US010646327B2

(12) United States Patent
Lund

(10) Patent No.: US 10,646,327 B2
(45) Date of Patent: May 12, 2020

(54) SELF-LOCKING SUTURE CONSTRUCTS AND METHODS OF TISSUE FIXATION

(71) Applicant: ARTHREX, INC., Naples, FL (US)

(72) Inventor: Jereme J. Lund, Ingleside, IL (US)

(73) Assignee: ARTHREX, INC., Naples, FL (US)

( * ) Notice: Subject to any disclaimer, the term of this patent is extended or adjusted under 35 U.S.C. 154(b) by 136 days.

(21) Appl. No.: 15/883,358

(22) Filed: Jan. 30, 2018

(65) Prior Publication Data

US 2018/0221133 A1 Aug. 9, 2018

Related U.S. Application Data

(60) Provisional application No. 62/457,099, filed on Feb. 9, 2017, provisional application No. 62/459,353, filed on Feb. 15, 2017, provisional application No. 62/481,055, filed on Apr. 3, 2017.

(51) Int. Cl.
*A61F 2/08* (2006.01)
*A61B 17/04* (2006.01)
*A61B 17/00* (2006.01)

(52) U.S. Cl.
CPC ........ *A61F 2/0811* (2013.01); *A61B 17/0401* (2013.01); *A61B 2017/00477* (2013.01); *A61B 2017/0404* (2013.01); *A61B 2017/0409* (2013.01); *A61B 2017/0459* (2013.01); *A61B 2017/0464* (2013.01); *A61F 2002/0852* (2013.01); *A61F 2002/0882* (2013.01); *A61F 2220/0075* (2013.01)

(58) Field of Classification Search
CPC ............... A61F 2/0811; A61B 17/0401; A61B 2017/0464; A61B 2017/00477; A61B 2017/0459; A61B 2017/0404; A61B 2017/0409
See application file for complete search history.

(56) References Cited

U.S. PATENT DOCUMENTS

| | | |
|---|---|---|
| 4,187,558 A | 2/1980 | Dahlen et al. |
| 4,301,551 A | 11/1981 | Dore et al. |
| 4,776,851 A | 10/1988 | Bruchman et al. |
| 4,790,850 A | 12/1988 | Dunn et al. |
| 4,792,336 A | 12/1988 | Hlavacek et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |
| 5,129,902 A | 7/1992 | Goble et al. |
| 5,171,274 A | 12/1992 | Fluckiger et al. |
| 5,211,647 A | 5/1993 | Schmieding |
| 5,217,495 A | 6/1993 | Kaplan et al. |
| 5,263,984 A | 11/1993 | Li et al. |
| 5,266,075 A | 11/1993 | Clark et al. |
| 5,306,301 A | 4/1994 | Graf et al. |

(Continued)

*Primary Examiner* — Katherine M Rodjom
(74) *Attorney, Agent, or Firm* — Potomac Law Group PLLC

(57) ABSTRACT

Knotless self-locking constructs and methods of tissue repairs. A flexible coupler creates a plurality of closed, knotless, continuous, adjustable, flexible loops having adjustable perimeters, the loops being located between a loop interconnection and two terminal ends. A weave region having an accordion configuration and a plurality of locking points is provided between each terminal end and each closed, knotless, continuous, adjustable, flexible loop.

14 Claims, 23 Drawing Sheets

(56) References Cited

U.S. PATENT DOCUMENTS

| | | |
|---|---|---|
| 5,320,626 A | 6/1994 | Schmieding |
| 5,397,357 A | 3/1995 | Schmieding et al. |
| 5,562,669 A | 10/1996 | McGuire |
| 5,575,819 A | 11/1996 | Amis |
| 5,628,756 A | 5/1997 | Barker, Jr. et al. |
| 5,643,266 A | 7/1997 | Li |
| 5,645,588 A | 7/1997 | Graf et al. |
| 5,931,869 A | 8/1999 | Boucher et al. |
| 5,961,520 A | 10/1999 | Beck, Jr. et al. |
| 5,964,764 A | 10/1999 | West, Jr. et al. |
| 6,296,659 B1 | 10/2001 | Foerster |
| 6,517,578 B2 | 2/2003 | Hein |
| 6,533,802 B2 | 3/2003 | Bojarski et al. |
| 7,097,654 B1 | 8/2006 | Freedland |
| 7,494,506 B2 | 2/2009 | Brulez et al. |
| 7,601,165 B2 | 10/2009 | Stone |
| 7,658,751 B2 | 2/2010 | Stone et al. |
| 7,686,838 B2 | 3/2010 | Wolf et al. |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,855 B2 | 11/2010 | Ellis et al. |
| 7,875,058 B2 | 1/2011 | Holmes, Jr. |
| 7,905,903 B2 | 3/2011 | Stone et al. |
| 7,909,851 B2 | 3/2011 | Stone et al. |
| 7,914,539 B2 | 3/2011 | Stone et al. |
| 7,959,650 B2 | 6/2011 | Kaiser et al. |
| 7,981,139 B2 | 7/2011 | Martin et al. |
| 8,088,130 B2 | 1/2012 | Kaiser et al. |
| 8,109,965 B2 | 2/2012 | Stone et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 8,298,262 B2 | 10/2012 | Stone et al. |
| 8,303,604 B2 | 11/2012 | Stone et al. |
| 8,361,113 B2 | 1/2013 | Stone et al. |
| 8,460,379 B2 | 6/2013 | Albertorio et al. |
| 8,562,645 B2 | 10/2013 | Stone et al. |
| 8,628,573 B2 | 1/2014 | Roller et al. |
| 8,652,171 B2 | 2/2014 | Stone et al. |
| 8,672,968 B2 | 3/2014 | Stone et al. |
| 8,926,662 B2 | 1/2015 | Perriello et al. |
| 8,951,286 B2 | 2/2015 | Sugimoto et al. |
| 9,017,381 B2 | 4/2015 | Kaiser et al. |
| 9,078,644 B2 | 7/2015 | Stone |
| 9,107,653 B2 | 8/2015 | Sullivan |
| 9,179,950 B2 | 11/2015 | Zajac et al. |
| 9,314,241 B2 | 4/2016 | Stone et al. |
| 9,332,979 B2 | 5/2016 | Sullivan et al. |
| 9,421,008 B2 | 8/2016 | Burkhart et al. |
| 9,445,803 B2 | 9/2016 | Marchand et al. |
| 9,463,013 B2 | 10/2016 | Pilgeram et al. |
| 9,486,211 B2 | 11/2016 | Stone et al. |
| 9,492,158 B2 | 11/2016 | Stone et al. |
| 9,498,204 B2 | 11/2016 | Denham et al. |
| 9,504,462 B2 | 11/2016 | Dooney et al. |
| 9,539,003 B2 | 1/2017 | Stone et al. |
| 9,572,655 B2 | 2/2017 | Denham et al. |
| 9,615,821 B2 | 4/2017 | Sullivan |
| 9,801,708 B2 | 10/2017 | Denham et al. |
| 9,833,230 B2 | 12/2017 | Stone |
| 10,004,493 B2 | 6/2018 | Stone et al. |
| 10,092,288 B2 | 10/2018 | Denham et al. |
| 10,265,060 B2 | 4/2019 | Dooney et al. |
| 10,368,855 B2 | 8/2019 | Burkhart |
| 10,398,426 B2 | 9/2019 | Burkhart et al. |
| 2007/0010857 A1 | 1/2007 | Sugimoto et al. |
| 2007/0185532 A1 | 8/2007 | Stone et al. |
| 2009/0076547 A1 | 3/2009 | Sugimoto et al. |
| 2010/0268273 A1* | 10/2010 | Albertorio ......... A61B 17/0401 606/232 |
| 2011/0208239 A1* | 8/2011 | Stone ................ A61B 17/0469 606/228 |
| 2011/0270278 A1 | 11/2011 | Overes et al. |
| 2012/0109194 A1 | 5/2012 | Miller et al. |
| 2012/0197271 A1 | 8/2012 | Astorino et al. |
| 2012/0239085 A1 | 9/2012 | Schlotterback et al. |
| 2013/0096611 A1 | 4/2013 | Sullivan |
| 2013/0110165 A1 | 5/2013 | Burkhart et al. |
| 2013/0345750 A1 | 12/2013 | Sullivan |
| 2014/0052179 A1 | 2/2014 | Dreyfuss et al. |
| 2015/0141995 A1 | 5/2015 | Norton |
| 2016/0007989 A1 | 1/2016 | Overes et al. |
| 2017/0035412 A1 | 2/2017 | Dooney et al. |
| 2017/0049434 A1 | 2/2017 | Dooney et al. |
| 2017/0105716 A1 | 4/2017 | Burkhart |
| 2018/0296207 A1 | 10/2018 | Burkhart et al. |

\* cited by examiner

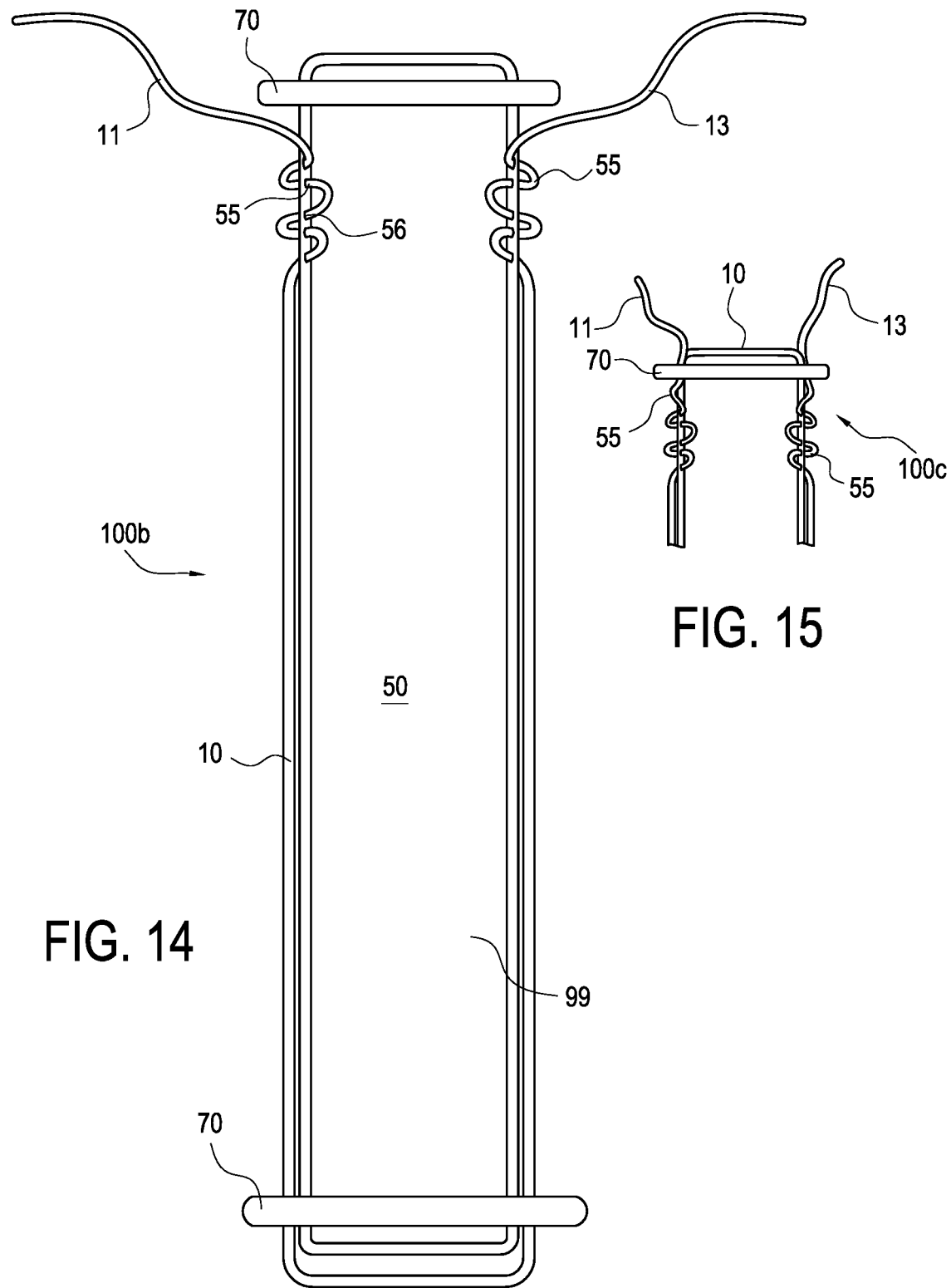

SELF-LOCKING SUTURE CONSTRUCTS AND METHODS OF TISSUE FIXATION

CROSS-REFERENCE TO RELATED APPLICATIONS

This application claims the benefit of U.S. Provisional Application No. 62/457,099 filed Feb. 9, 2017; U.S. Provisional Application No. 62/459,353, filed Feb. 15, 2017; and U.S. Provisional Application No. 62/481,055, filed Apr. 3, 2017, the disclosures of all of which are incorporated by reference in their entireties herein.

BACKGROUND

The disclosure relates to surgical devices and, more specifically, to knotless self-locking suture constructs and associated methods of tissue repairs.

SUMMARY

Knotless self-locking constructs and methods of tissue repairs are disclosed. A self-locking construct can create a knotless, self-locking repair. A flexible coupler foils a plurality of closed, knotless, continuous, adjustable, flexible loops having adjustable perimeters, the loops being located between a loop interconnection and two terminal ends. A weave region having an accordion configuration and a plurality of locking points is provided between each terminal end and each closed, knotless, continuous, adjustable, flexible loop. A self-locking construct can be knotless. A self-locking construct may be employed to re-attach normal anatomical structures, i.e., a first tissue to a second tissue, such as soft tissue, tendon, ligament, and/or bone, to each other and/or any combination of one another, by employing a self-locking mechanism. If more than one flexible coupler is employed, the flexible couplers may be similar or dissimilar and may have similar—or different configurations and/or colors and/or coatings. The flexible couplers may be sutures and/or tapes. A self-locking construct may be employed as a stand-alone construct or with additional fixation devices, for example, attached to one or more buttons.

A self-locking mechanism and implant construct for knotless self-locking repairs such as knotless attachment of first tissue to second tissue (for example, bone to bone or soft tissue to bone) is disclosed. The implant construct may be an orthopedic implant construct. The construct is formed of one single continuous flexible coupler. Two terminal ends are run in opposite direction of one another to form at least two flexible, continuous, knotless, closed, adjustable loops, each having an adjustable perimeter. Each of the terminal ends is then woven through the flexible coupler, back and through in the opposite direction multiple times, to form an accordion-style weave that creates multiple locking points to lock the two flexible loops. Both ends then exit the flexible coupler. The construct may be shrunk when both terminal ends are pulled. The construct may be attached to one or more fixation devices.

A self-locking suture button construct for knotless self-locking repairs is disclosed. The self-locking suture construct includes two flexible couplers of either round or flat design that are run through a fixation device, for example, implant, anchor, screw, plate, button, etc. The flexible couplers may include suture and/or may be formed of suture. The flexible couplers create a loop run through and/or around the implant in either an opposing parallel fashion, or passed around/through one another creating two flexible, continuous, adjustable, knotless, closed suture loops with adjustable perimeters. A terminal end of each of the two loops (ends 1 and 2) is each run back through the flexible coupler in an accordion/pleat weave and/or Chinese trap fashion to complete the loop(s), and create friction locking points. The other terminal ends (3 and 4) of the flexible coupler in which ends 1 and 2 are woven through, are used to stitch and secure tissue to other tissue, for example, soft tissue to bone. The implant may be secured to tissue. Tension may then be applied to ends 1 and 2 to shrink/close the loops bringing the button and tendon/ligament/and/car soft tissues (ends 3 and 4) together while locking the construct in place.

An accordion-pleat weave self-locking suture mechanism for knotless self-locking repairs such as knotless attachment of first tissue to second tissue is disclosed. A flexible coupling creates a locking mechanism (pleat/accordion weave) that is locked when counter traction is applied to both ends of the flexible coupling that the flexible coupling is woven through. The free ends exiting the flexible coupling can be pulled to shrink the construct, thus applying a counter traction to the flexible coupling that the ends are woven in pleat/accordion fashion through. A flexible coupling may be a flat/tape flexible coupling (suture and/or suture tape). The flexible coupling may be attached to one or more fixation devices, for example, anchors, screws, implants, buttons, etc. At least one of the buttons may be an implantable button or a cortical button.

Methods of self-locking tissue repairs are also disclosed. A first tissue is approximated to a second tissue with a knotless self-locking surgical construct that includes a self-locking tensionable construct with a self-locking mechanism. In an embodiment, a flexible coupler forms at least two flexible, continuous, knotless, closed, adjustable loops having adjustable perimeters with its terminal ends. Each of the terminal ends is woven through the flexible coupler, back and through in the opposite direction multiple times to form an accordion-style weave region that creates multiple locking points to lock the at least two flexible loops. Both ends exit the flexible coupler. The construct may be shrunk when both terminal ends are pulled.

BRIEF DESCRIPTION OF THE DRAWINGS

FIG. 14 illustrates a surgical construct according to another exemplary embodiment.

FIG. 15 is an enlarged view of the coupling tails of the surgical construct of FIG. 14 (and with the tails passed through one of the fixation devices).

DETAILED DESCRIPTION

Figure 1:
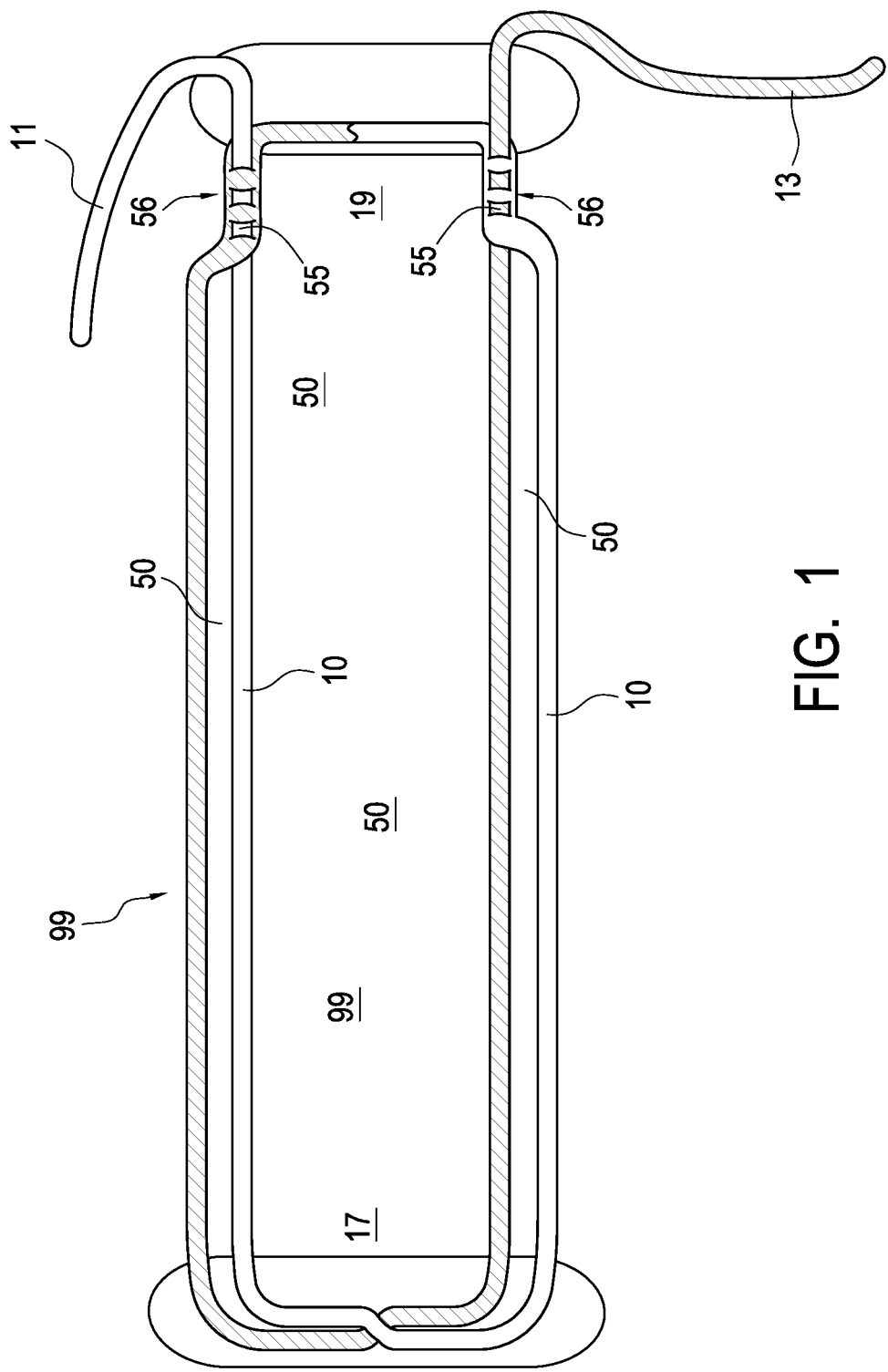
FIG. 1 illustrates a self-locking tensionable construct.

The disclosure provides surgical self-locking adjustable loop constructs, self-locking suture loop mechanisms, and methods for securing a first tissue to a second tissue (for example, soft tissue to bone, or bone to bone) with a tensionable construct including at least two adjustable, knotless, flexible, closed loops and a self-locking mechanism. The tensionable construct is a locking mechanism/construct that includes at least two adjustable, knotless, flexible, continuous, closed loops and has the ability to securely lock flexible couplers, for example, suture tapes or strands. The surgical constructs include a self-locking tensionable construct attached to one or more fixation devices, for example, one or more anchors, implants, buttons, screws, plates, etc., or combinations thereof.

In one embodiment, the disclosure provides a self-locking suture weave construct. An orthopedic implant construct is utilized to attach or re-attach normal anatomical structures, tissue to tissue, bone to bone, and/or bone to soft tissue. The construct may be composed of one single continuous flexible coupler in the form of suture, round, and/or flat suture. Two terminal ends are run in opposition of one another to compose two suture loops, the terminal ends are then woven through the flexible coupler, back and through in the opposite direct multiple times to form an accordion style weave that creates multiple locking points to lock the two suture loops. Both ends then exit the flexible coupler. The construct can be shrunk when both terminal ends are pulled.

In another embodiment, the disclosure provides a self-locking suture button construct. The self-locking suture construct includes two flexible couplers of either round or flat design that are run through an implantable button. The flexible couplers may include suture and/or may be formed of suture. The flexible couplers create a loop run through and/or around the button in either an opposing parallel fashion, or passed around/through one another creating two suture loops. One terminal end of each loops (ends 1 and 2) are run back through the suture in an accordion/pleat weave and/or Chinese trap fashion to complete the loop(s), and create friction locking points. The other terminal ends (3 and 4) of the flexible coupler in which ends 1 and 2 are woven through, are used to stitch and secure a tendon, ligament, and/or soft tissue. The button is inserted in bone either unicortically or hi-cortically. Tension is then applied to ends 1 and 2 to shrink/close the loops bringing the button and tendon/ligament/and/or soft tissues (ends 3 and 4) together while locking the construct in place.

In yet another embodiment, the disclosure provides an accordion pleat weave self-locking suture mechanism and construct. The self-locking mechanism may be employed for attaching soft tissue, tendon, ligament, and/or bone, to each other and/or any combination of one another, where a flat/tape flexible coupling (suture) creates a pleat/accordion weave that is locked when counter traction is applied to both ends of the flexible coupling that the flexible coupling (suture) is woven through. The free ends exiting the flexible coupler (suture) can be pulled to shrink the construct, thus applying a counter traction to the flexible coupler (suture) that the ends are woven in pleat/accordion fashion through.

The flexible couplers may include any flexible materials, strands or ribbons such as suture or tape, for example, multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein) FiberWire® suture is formed of an advanced, high-strength fiber material, namely ultra-high molecular weight polyethylene (UHMWPE), sold under the tradenames Spectra (Honeywell) and Dyneema (DSM), braided with at least one other fiber, natural or synthetic, to form lengths of suture material.

The flexible couplers may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical self-locking constructs can be used with any type of flexible material or suture known in the art.

Methods of self-locking tissue repairs are also disclosed. In an embodiment, at least one flexible coupler is looped to form a self-locking loop construct with at least two knotless, continuous, flexible, closed adjustable loops having an adjustable perimeter; a loop interconnection; and two terminal ends. Each terminal end is passed through different points spaced apart a length of the flexible coupler and a distance away from the loop interconnection, to form first and second pleat/accordion weave regions with first and second pluralities of locking points, respectively. The terminal ends may be slidably passed through the flexible coupler. The terminal ends may be passed through the flexible coupler at different separate points, beginning with a first point and then passing the terminal end through another, second point (at a position adjacent the first point) to form the first and second loops and the first and second pleat/accordion weave regions with the first and second plurality of locking points. When the terminal ends are pulled, the construct shrinks, i.e., the perimeters of the first and the second loops decrease. The distance between the first and second locking points may also decrease. The tensionable construct allows the user (for example, surgeon) to control the tension of the flexible coupler on first tissue (for example, soft tissue) to be attached to a second tissue (for example, bone).

The surgical constructs and methods of the present disclosure provide self-locking mechanisms, self-locking tensionable constructs and surgical constructs, as well as methods for tissue repair, for example, attachment of a first tissue to a second tissue, such as soft tissue to bone, with such constructs.

Figure 2:
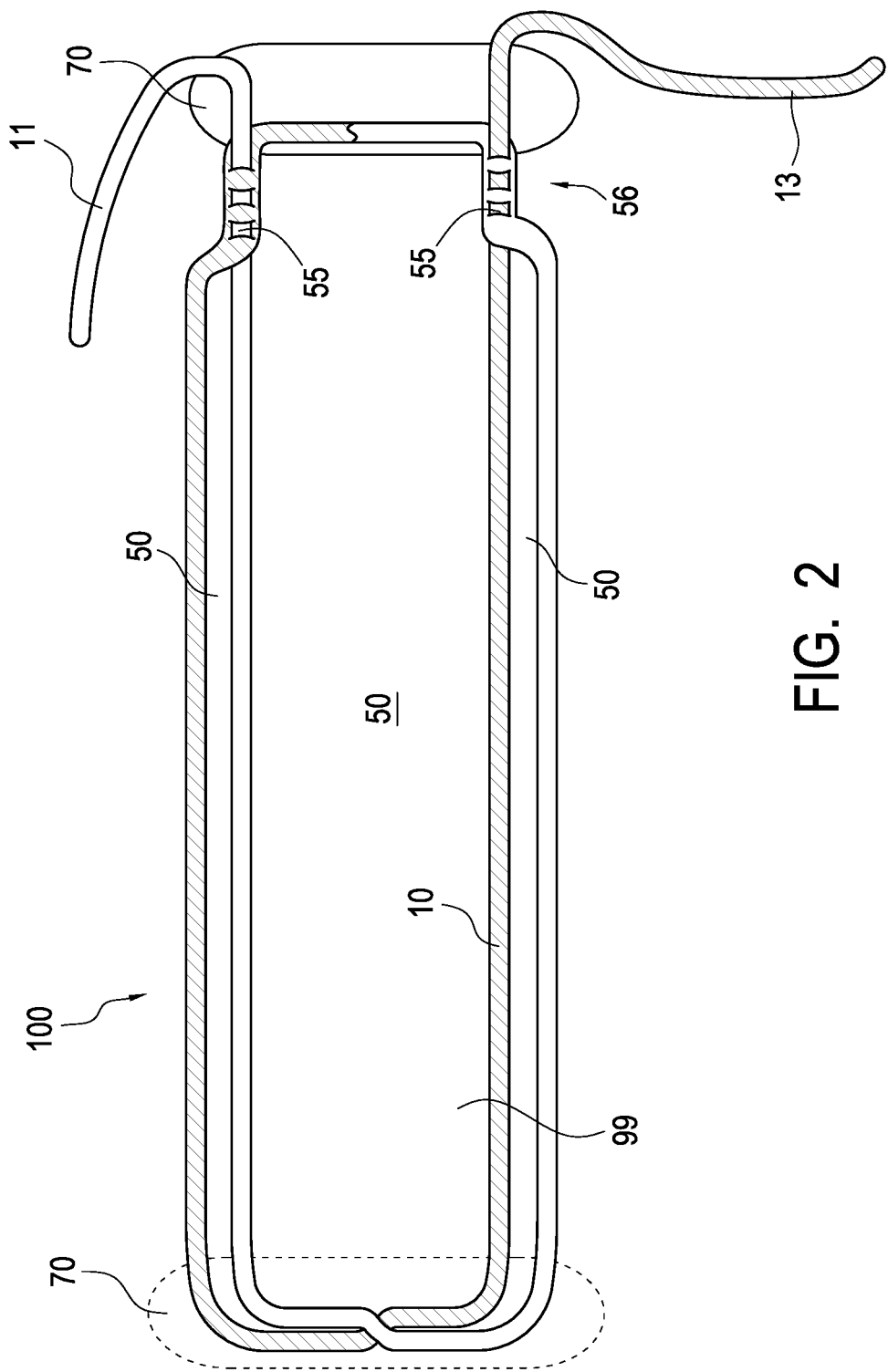
FIG. 2 illustrates a surgical construct according to an exemplary embodiment.

Referring now to the drawings, where like elements are designated by like reference numerals, FIGS. 1-7 illustrates structural components of self-locking tensionable construct 99, 199, 299, 299a that may be employed by itself or in conjunction with additional fixation devices, for example, anchors, implants, or buttons, to form surgical constructs. FIG. 2 illustrates an exemplary surgical construct 100 with the exemplary self-locking tensionable construct 99 of FIG. 1. FIGS. 5-15, 24 and 25 illustrate additional embodiments of surgical constructs 100a, 100b, 100c, 100d, 100e, 100f, 200, 200a, 300, 300a. FIGS. 16-23 and 26 illustrate steps of various methods of tissue repair with the surgical constructs of the disclosure.

Self-locking tensionable construct 99, 199, 299, 299a of FIGS. 1-7 is a self-locking adjustable loop construct. Self-locking tensionable construct 99, 199, 299, 299a is a self-locking suture weave construct in the form of an orthopedic implant construct which may be utilized to attach or re-attach a first tissue to a second tissue, for example, normal anatomical structures, bone to bone, tissue to tissue, and/or bone to tissue, among others.

Figure 4:
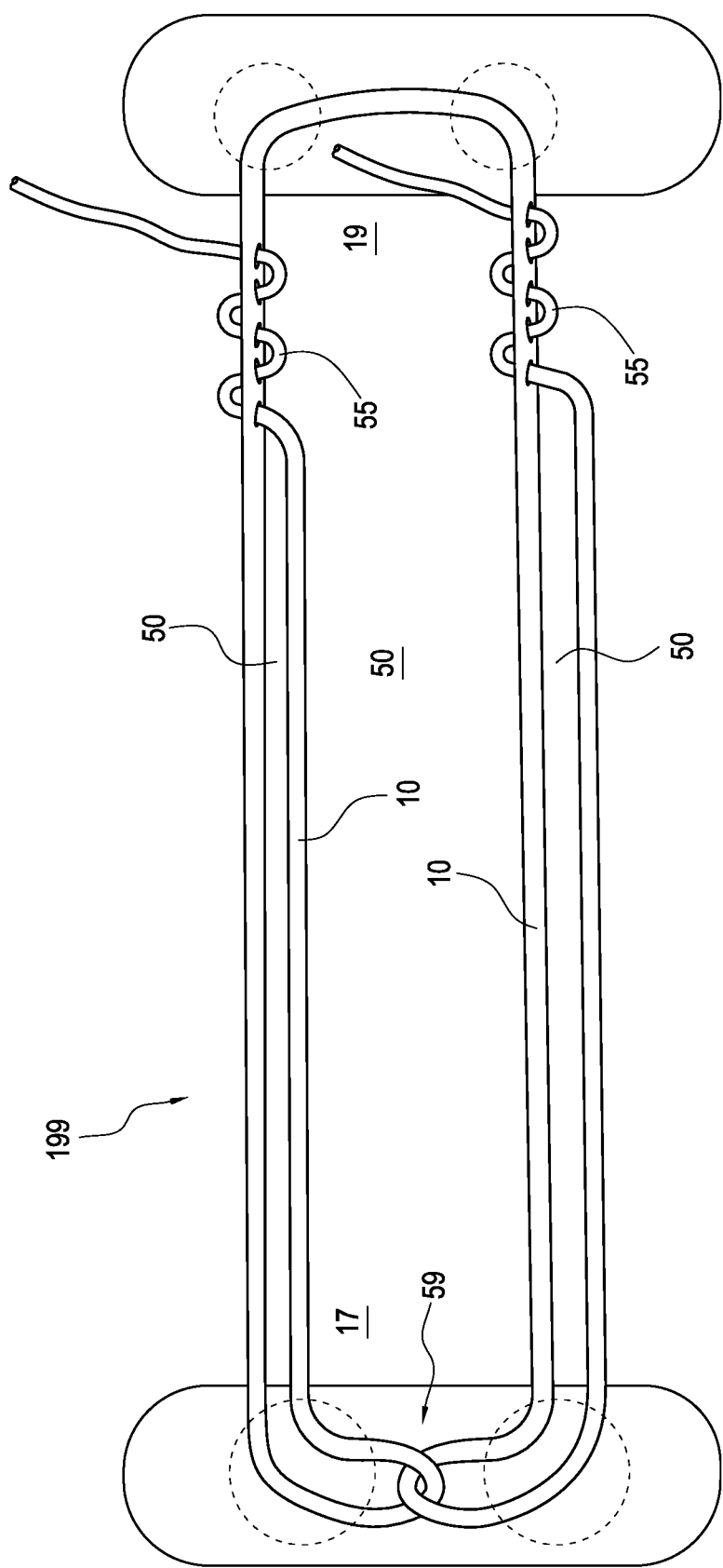
FIG. 4 illustrates another self-locking tensionable construct.

Self-locking tensionable construct 99, 199 is formed of one single continuous flexible coupler 10 (flexible material 10 or flexible strand 10 or flexible tape 10) in form of suture, either round and/or flat suture, for example, suture tape. The flexible coupler 10 is provided with two terminal ends, a first end 11 and a second end 13. The two terminal ends 11, 13 are run in opposition of one another to form at least two suture loops 50. The self-locking tensionable construct 199 shown in FIG. 4 also includes interconnection 59 (loop interconnection 59 or intertwined region 59) formed by the flexible coupler 10. The at least two loops 50 are flexible, closed, knotless, continuous, adjustable loops each having an adjustable perimeter. Interconnection 59 is located at one end of the construct, for example, at a first loop end 17 (FIG. 4).

Figure 3:
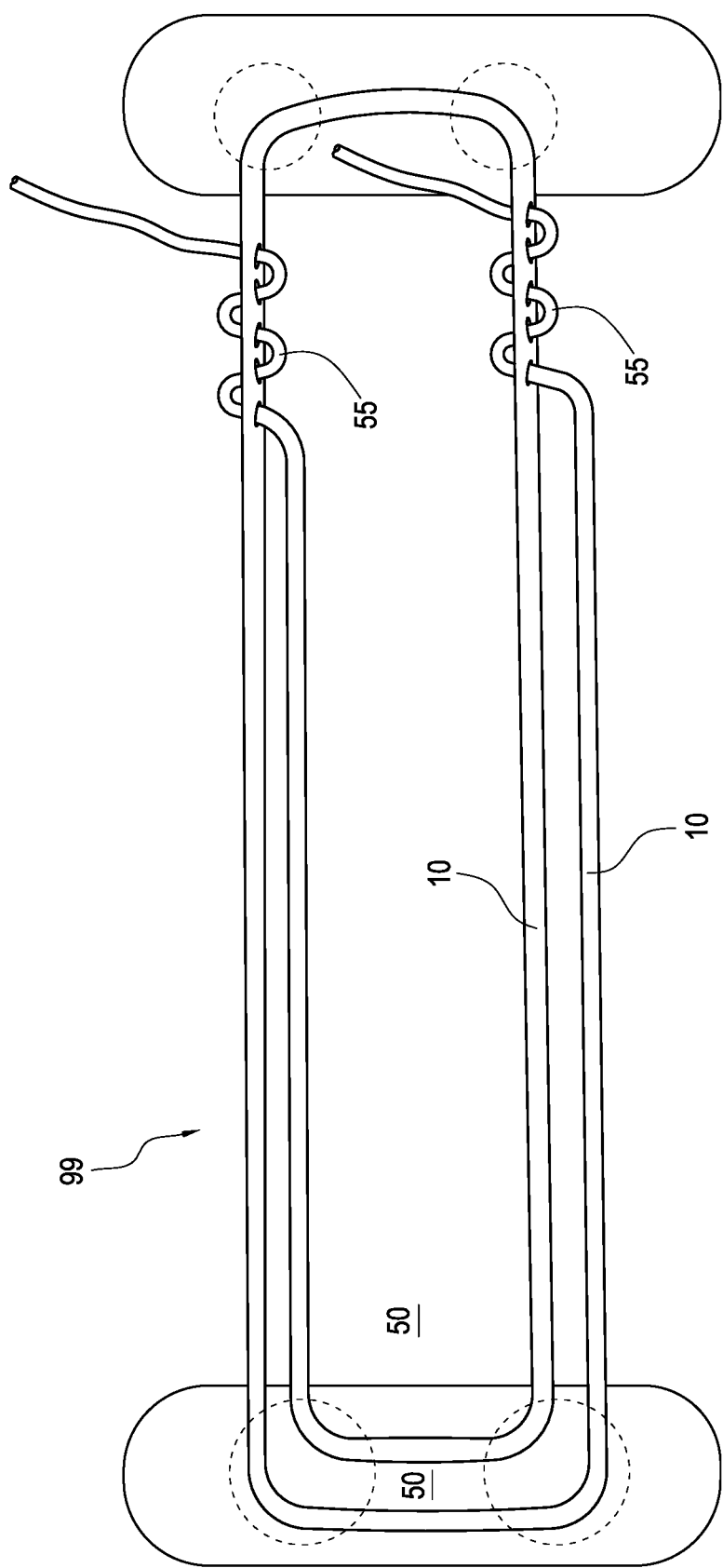
FIG. 3 is another view of the self-locking tensionable construct of FIG. 1.

The terminal ends 11, 13 are woven through the flexible coupler 10, back and through in the opposite direction multiple times, to each form an accordion style weave region 55 that creates multiple locking points 56 that lock the two suture loops 50. The two accordion-style weave regions 55 and the plurality of locking points 56 may be located at an end opposite the end where the interconnection 59 is located, for example, at a second loop end 19. Both ends 11, 13 then exit the flexible coupler 10 at the second loop end 19. The self-locking tensionable construct 99, 199 can be shrunk when both terminal ends 11, 13 are pulled to decrease the perimeter of at least one of the flexible, closed, knotless, adjustable loops 50. FIGS. 1 and 3 illustrate two flexible, closed, knotless, continuous, adjustable loops 50 each having an adjustable perimeter, as part of self-locking tensionable construct 99. FIG. 4 illustrates three flexible, closed, knotless, continuous, adjustable loops 50 each having an adjustable perimeter, as part of self-locking tensionable construct 199.

Figure 8:
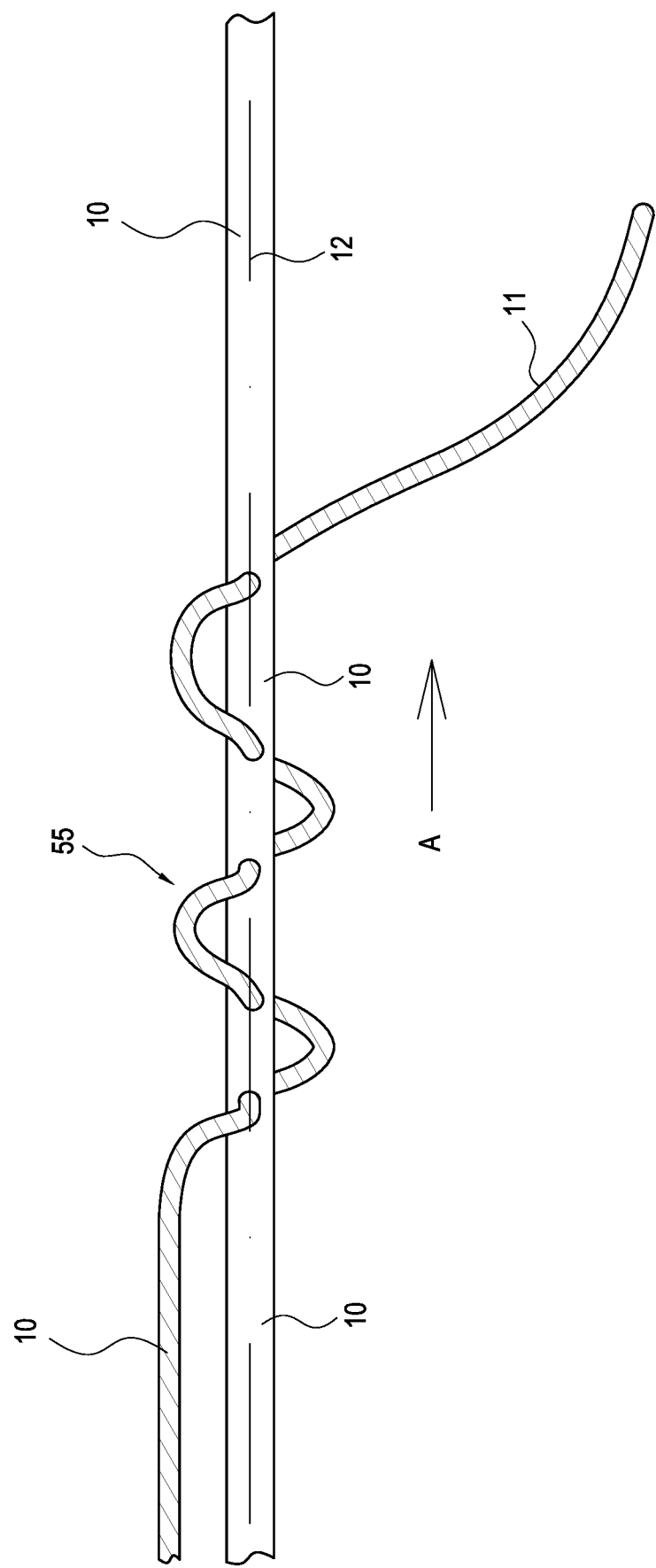
FIG. 8 is an enlarged view of an accordion-style weave region of the self-locking tensionable construct of FIG. 1.

As shown in more detail in FIG. 8, one of the free ends, for example, free terminal end 11 is passed through the flexible coupler 10 multiple times (for example, five times at five different points) along longitudinal axis 12 of the flexible coupler 10, and in direction A, to form first accordion style weave region 55. The other terminal end, for example, free terminal end 13 is also passed through the flexible coupler 10 multiple times, also along longitudinal axis 12 of the flexible coupler 10 and in a direction parallel to direction A, and in same sense/direction, to form second accordion style weave region 55. Each free terminal end 11, 13 is passed from a first surface of the flexible coupler 10 to a second, opposite surface of the flexible coupler 10, and for a plurality of times, to form locking points 56 of the first and second accordion style weave regions 55.

Self-locking tensionable construct 99, 199, 299, 299a may be provided as a stand-alone surgical construct or, alternatively, may be provided already attached to one or more fixation devices, for example, one or more implantable buttons, or may be subsequently attached to one or more fixation devices. For example, and as detailed below, FIGS. 2, 11, 13 and 16-19 illustrate self-locking tensionable construct 99, 199 attached to a single fixation device to form surgical construct 100. FIGS. 9, 13-15 and 20-22 illustrate surgical constructs 100a, 110b, 100c, 100d, 100e, 100f wherein self-locking tensionable construct 99, 199 is coupled to two fixation devices, which may be similar or different from each other.

In embodiments where two or more flexible couplers are employed, the two or more flexible couplers also include at least one self-locking mechanism 299, 299a similar to self-locking tensionable construct 99, 199. In each instance, one terminal end of each of the flexible couplers is passed through itself to form an accordion-style weave region 55 for each flexible coupler. Constructs with two or more flexible couplers are illustrated in FIGS. 5-7, 10 and 23-26, for example.

FIG. 2 illustrates surgical construct 100 (self-locking construct 100; knotless self-locking construct 100; construct 100; knotless self-locking loop construct 100) formed of exemplary self-locking tensionable construct 99 attached to a fixation device 70, for example, a cortical button 70. Fixation device 70 may be a button or any similar structure that allows attachment to a flexible coupler and/or tissue to be fixated. Fixation device 70 may be any device that allows passing of the flexible couplers therethrough (for example, through a plurality of openings or apertures or passages formed within a body of the fixation device) to form a plurality of continuous, knotless, self-locking, flexible, adjustable loops 50. In an exemplary embodiment, the fixation device is a cortical button having a rectangular configuration that allows passage of the flexible coupler 10 (and optional formation of flexible coupler 5 interconnection 59).

Figure 5:
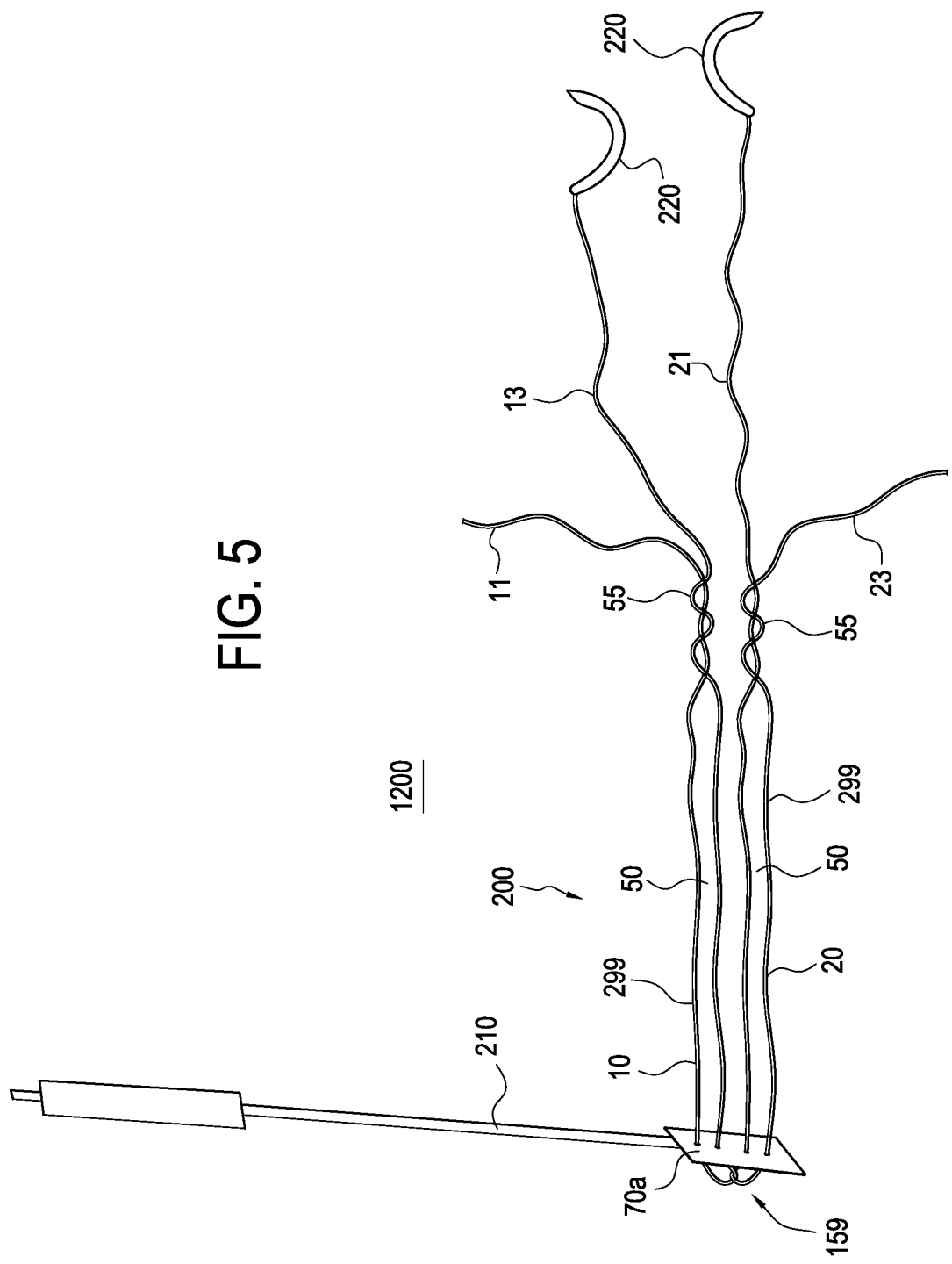
FIG. 5 illustrates a surgical assembly according to an exemplary embodiment.
Figure 6:
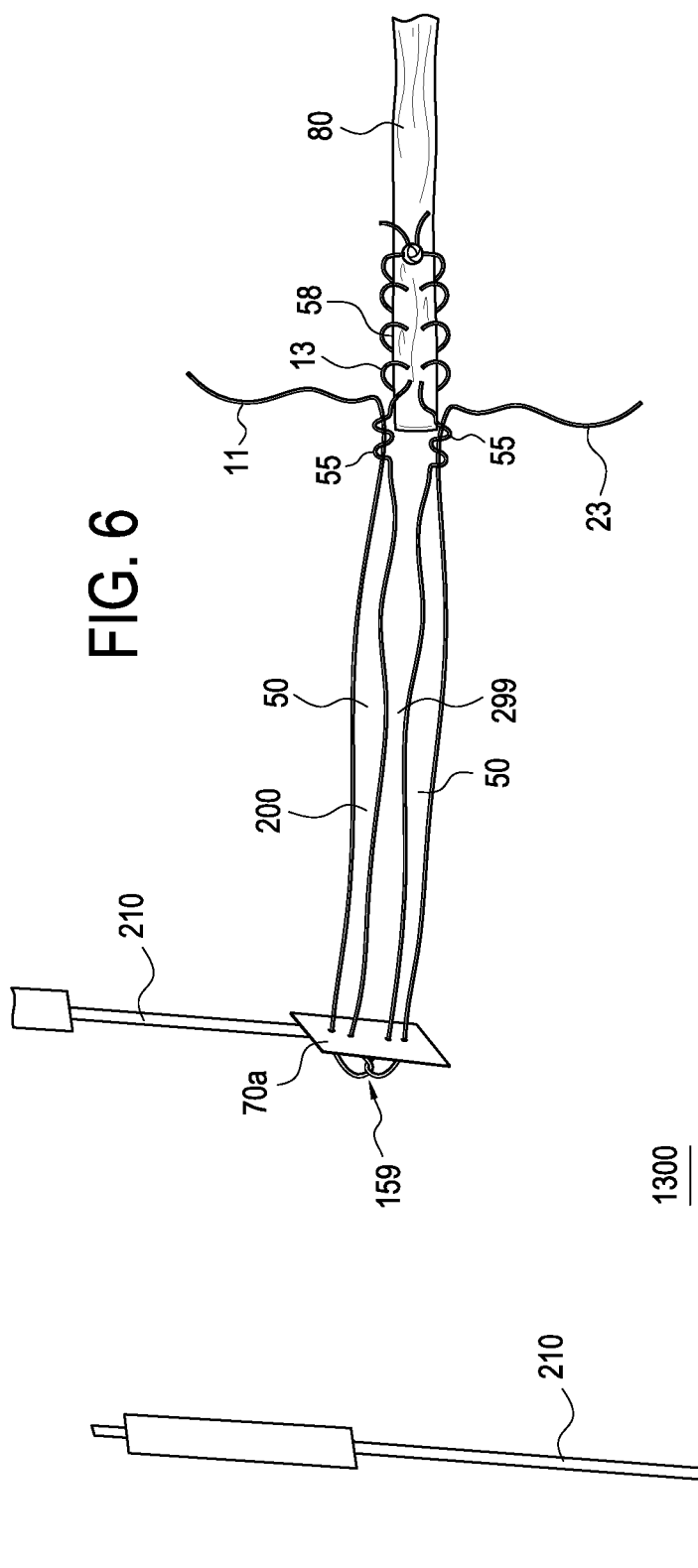
FIG. 6 illustrates the surgical assembly of FIG. 5 attached to tissue.
Figure 7:
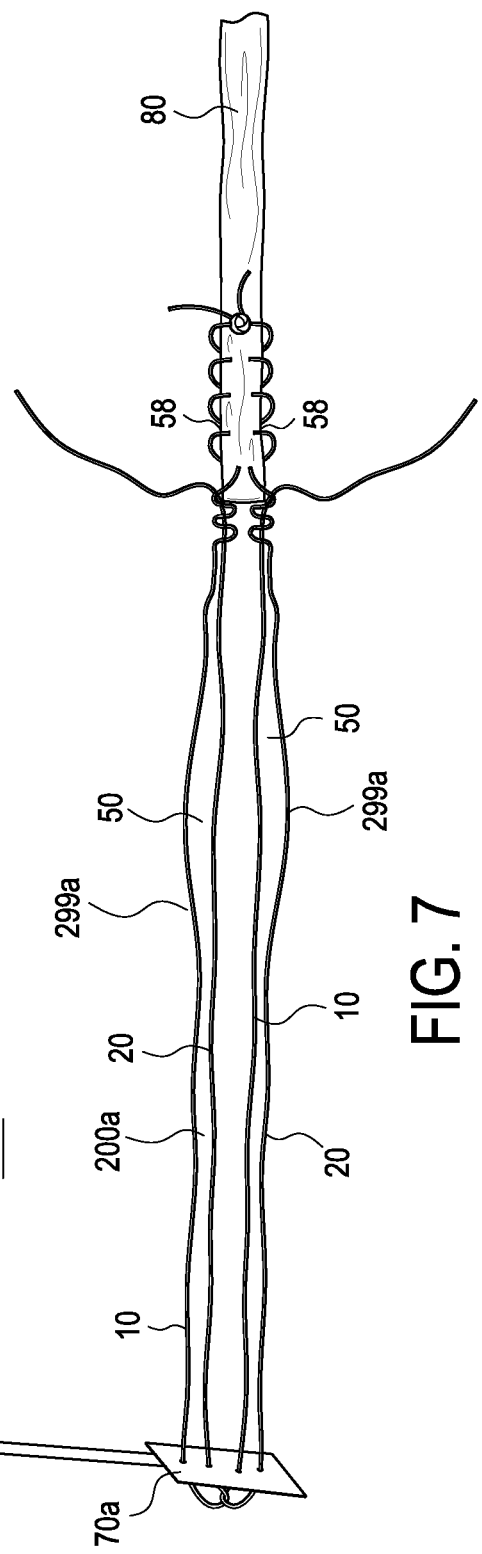
FIG. 7 illustrates a surgical assembly according to another exemplary embodiment and attached to tissue.

FIGS. 5-7 illustrate surgical assemblies 1200, 1300 (surgical systems 1200, 1300) with inserter 210 pre-loaded with surgical constructs 200, 200a. Surgical constructs 200, 200a are similar in part with construct 100 in that they also form continuous, flexible, knotless, adjustable loops 50 and contain accordion style weave regions 55 that create multiple locking points 56 to lock the two suture loops 50 as part of self-locking tensionable construct 299, 299a. Surgical constructs 200, 200a differ from construct 100 in that they contain two flexible couplers 10, 20, each provided with terminal ends 11, 13 and 21, 23, respectively.

FIG. 5 illustrates surgical assembly 1200 that includes inserter 210 attached to construct 200. Construct 200 includes at least two flexible couplers 10, 20 attached to fixation device 70a. One of the at least two flexible couplers 10, 20 is attached to a suturing/passing device 220 to allow passing of the flexible couplers 10, 20 through or around tissue 80. FIG. 5 illustrates exemplary end 13 of first flexible coupler 10 attached to exemplary needle 220, and exemplary end 21 of second flexible coupler 20 attached to another exemplary needle 220. The two exemplary suturing/passing devices 220 may be similar or different. Fixation device 70a may be a button or any similar structure that allows attachment to a flexible coupler and/or tissue to be fixated. In exemplary embodiments, fixation device 70a may be a button.

Fixation device 70a may be any device that allows passing of multiple flexible couplers therethrough (for example, through a plurality of openings or apertures or passages formed within a body of the fixation device) to form a plurality of continuous, knotless, self-locking, flexible, adjustable loops 50. In an exemplary embodiment, the fixation device is a cortical button having a slanted configuration that allows passage of the flexible couplers 10, 20 and formation of interconnection 159 (FIG. 6). Details of exemplary fixation device 70a and corresponding inserter/applicator 210 are set forth in U.S. Pat. No. 9,226,743 issued on Jan. 5, 2016, the disclosure of which is incorporated in its entirety herewith. As detailed in U.S. Pat. No. 9,226,743, fixation device 70a may have various configurations and/or geometries as long as its body is provided with a slanted surface area (side area) and a recess/cavity extending from the slanted surface area, and as long as the body provides attachment to flexible strand(s) and/or tissue. Button 70a may be an oblong button (shown schematically in FIGS. 5-7) designed with a small hole or cavity on the end of the button, to accept a threaded region of the inner shaft of the inserter/applicator 210 and to be placed at the tip of the inserter/applicator 210. FIGS. 5-7 illustrate inserter/applicator 210 with button 70a in the assembled state, i.e., inserter/applicator 210 is pre-loaded with button 70a.

Exemplary-only button 70a of FIGS. 5-7 has a general rectangular (oblong) configuration with both lateral sides slanted (non-vertical) and about parallel to each other. The disclosure is not limited to this embodiment, however, and contemplates fixation devices (buttons or similar structures) with only one side slanted or with any number of sides slanted. In addition, and as detailed below, the disclosure also contemplates additional buttons having a round or generally rectangular configuration without any slanted faces (such as fixation device 70, detailed below).

FIG. 6 illustrates the assembly of FIG. 5 after passage of ends 13, 21 through tissue 80 (tendon 80) to form free stitches 58. FIG. 7 illustrates surgical assembly 1300 (surgical system 1300) that includes inserter 210 attached to construct 200a. One end of the two flexible couplers 10, 20 is attached to a suturing/passing device to allow passing of the flexible couplers 10, 20 through or around tissue 80. FIG. 7 illustrates exemplary stitches 58 formed by first and second coupler 10, 20 in tissue 80. Fixation device 70a may be any structure that allows passing of the flexible couplers 10, 20 therethrough to form the plurality of continuous, self-locking, flexible, knotless, adjustable loops 50. In an exemplary-only embodiment and as illustrated in FIGS. 5-7, the fixation device is a cortical button having a slanted configuration that allows passage of the flexible couplers 10, 20 with or without formation of interconnection 159.

FIG. 8 illustrates an enlarged view of the locking points and suture weave region 55 with the flexible coupler 10 passed through itself multiple times. Flexible coupler 10 is in the form of a flat tape/suture. Free end 11 is pulled to shrink the self-locking tensionable construct 99, 199, 299, 299a. Applied counter traction allows locking of the construct by the self-locking mechanism. Each terminal end 11, 13 is passed through different points spaced apart a length of the flexible coupler and a distance away from the loop interconnection, to form a first and a second pleat/accordion weave region 55, with a first and a second plurality of locking points 56, respectively. The terminal ends 11, 13 may be slidably passed through the flexible coupler 10. The terminal ends may be passed through the flexible coupler at different separate points, beginning with a first point and then passing the terminal end through another, second point (at a position adjacent the first point) to form the first and second loops and the first and second pleat/accordion weave regions with the first and second plurality of locking points. When the terminal ends are pulled, the construct shrinks, i.e., the perimeters of the first and the second loops decrease. The distance between the first and second locking points may also decrease.

Construct 200, 200a of FIGS. 5-7 is a self-locking suture button construct. The self-locking suture construct 200, 200a includes at least two flexible couplers 10, 20 of either round or flat design that are run through a fixation device such as implantable button 70a. The flexible couplers 10, 20 may include suture and/or may be formed of suture and/or suture tape. The flexible couplers 10, 20 create a loop run through and/or around the button 70a in either an opposing parallel fashion, or passed around/through one another creating two suture loops 50. One terminal end of each loops (ends 1 and 2) are run back through the suture/flexible coupler 10, 20 in an accordion/pleat weave region 55 and/or Chinese trap fashion to complete the loop(s), and create friction locking points 56. The other terminal ends (3 and 4) of the flexible coupler 10, 20 in which ends 1 and 2 are woven through, are used to stitch and secure tissue 80, for example, a tendon, ligament, graft and/or soft tissue 80. The button 70a is inserted in bone either unicortically or bi-cortically. Tension is then applied to ends 1 and 2 to shrink/close the loops 50, bringing the button 70a and tendon/ligament/graft 80 (ends 3 and 4) together while locking the construct 200, 200a in place.

Figure 9:
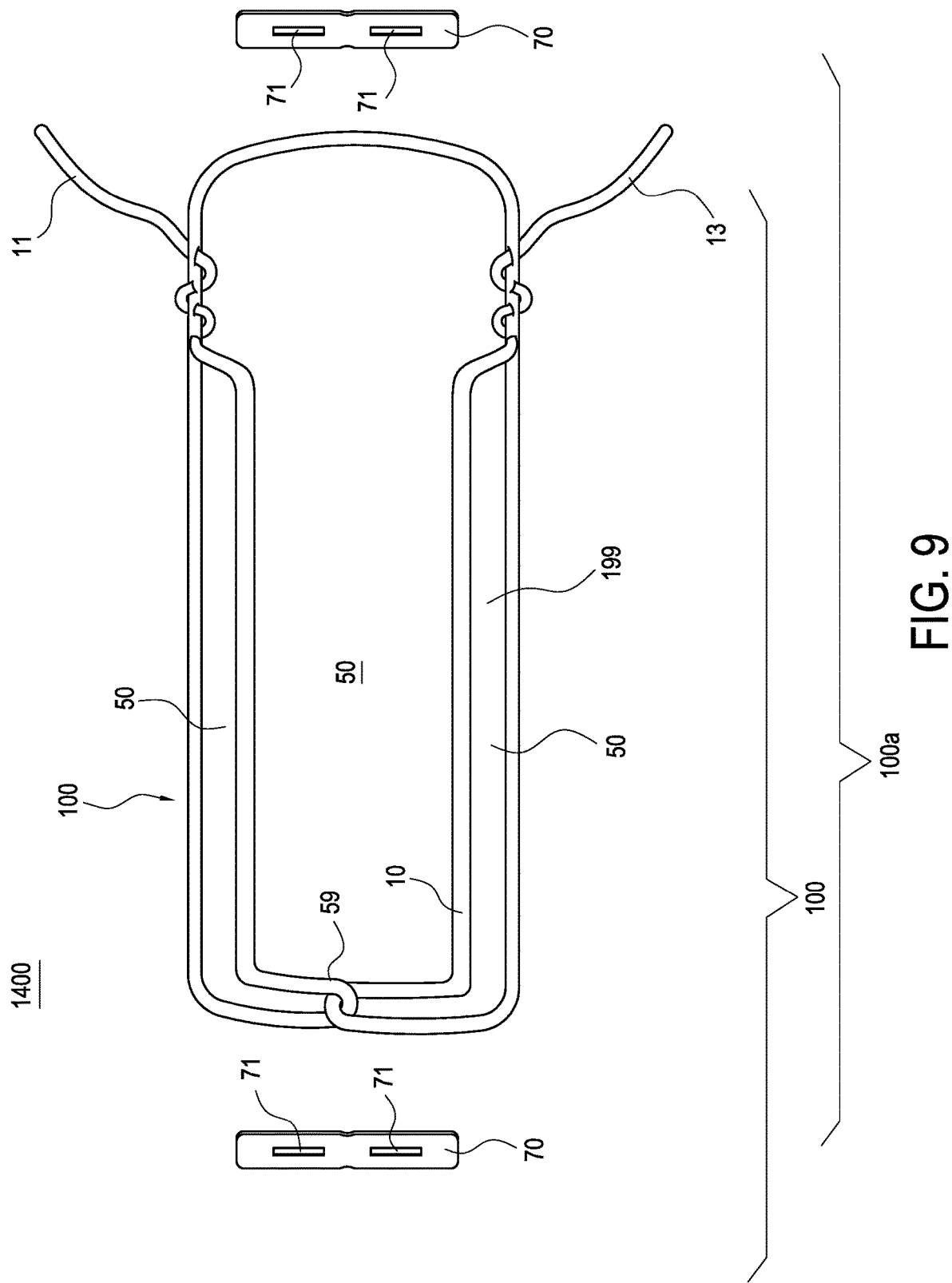
FIG. 9 illustrates the surgical construct of FIG. 2 in the disassembled state.
Figure 13:
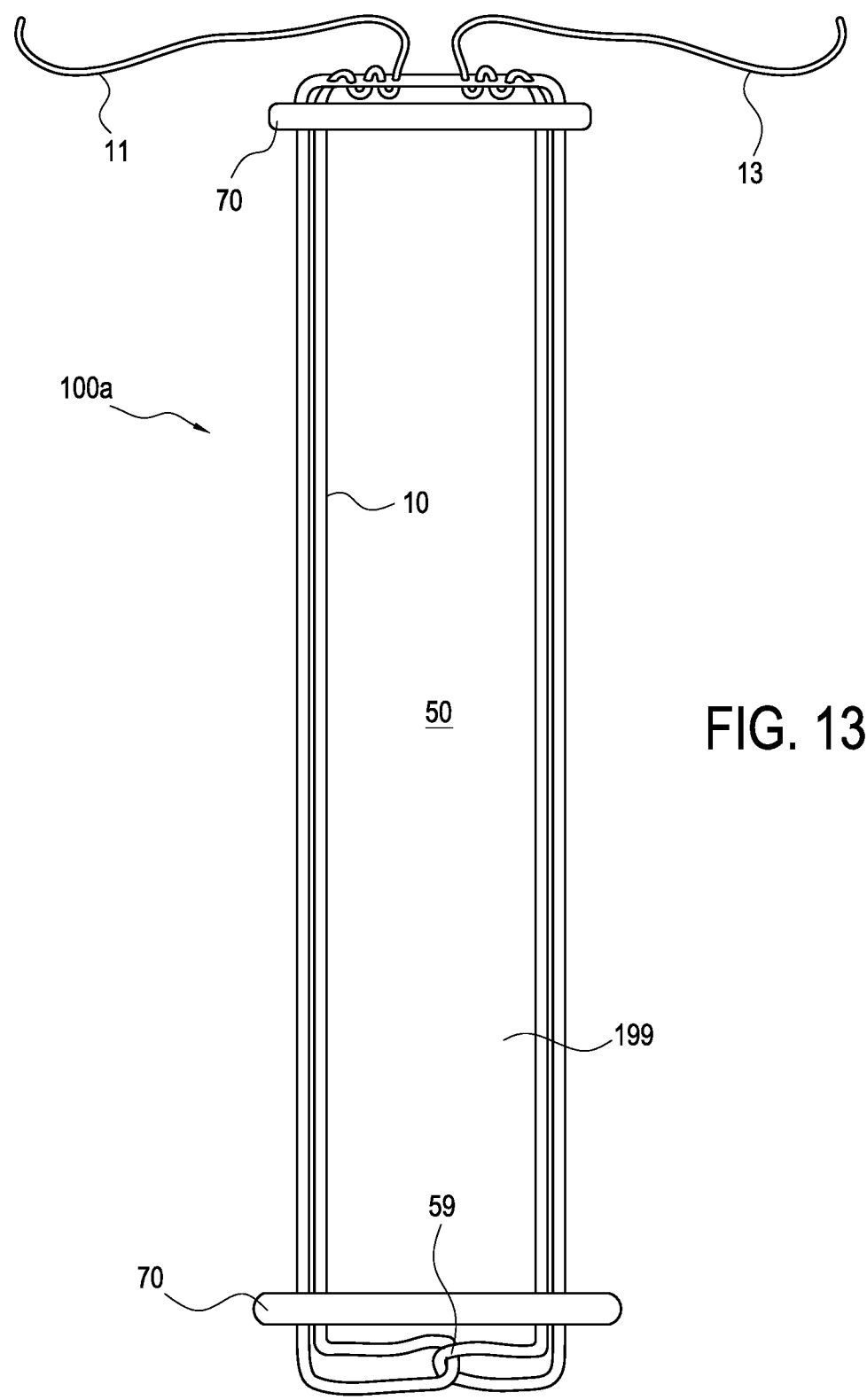
FIG. 13 illustrates a surgical construct according to another exemplary embodiment.

FIG. 9 illustrates surgical assembly 1400 with exemplary self-locking tensionable construct 199 adjacent a plurality of fixation devices 70 to form either construct 100 (FIG. 11) or construct 100a (FIG. 13). Fixation devices 70 may be cortical buttons with at least two holes/openings/passages 71 dimensioned to allow passage of the flexible coupler 10. At least one of the fixation devices 70 may be attached to self-locking tensionable construct 199. Fixation devices 70 may be similar or different, and may have various dimensions according to the intended surgical application. Self-locking tensionable construct 199 may also be attached to only one fixation device, for example to only one fixation device 70, and after the formation of the self-locking tensionable construct 199, i.e., by passing the ends 11, 13 through apertures 71 of the fixation device 70.

Figure 10:
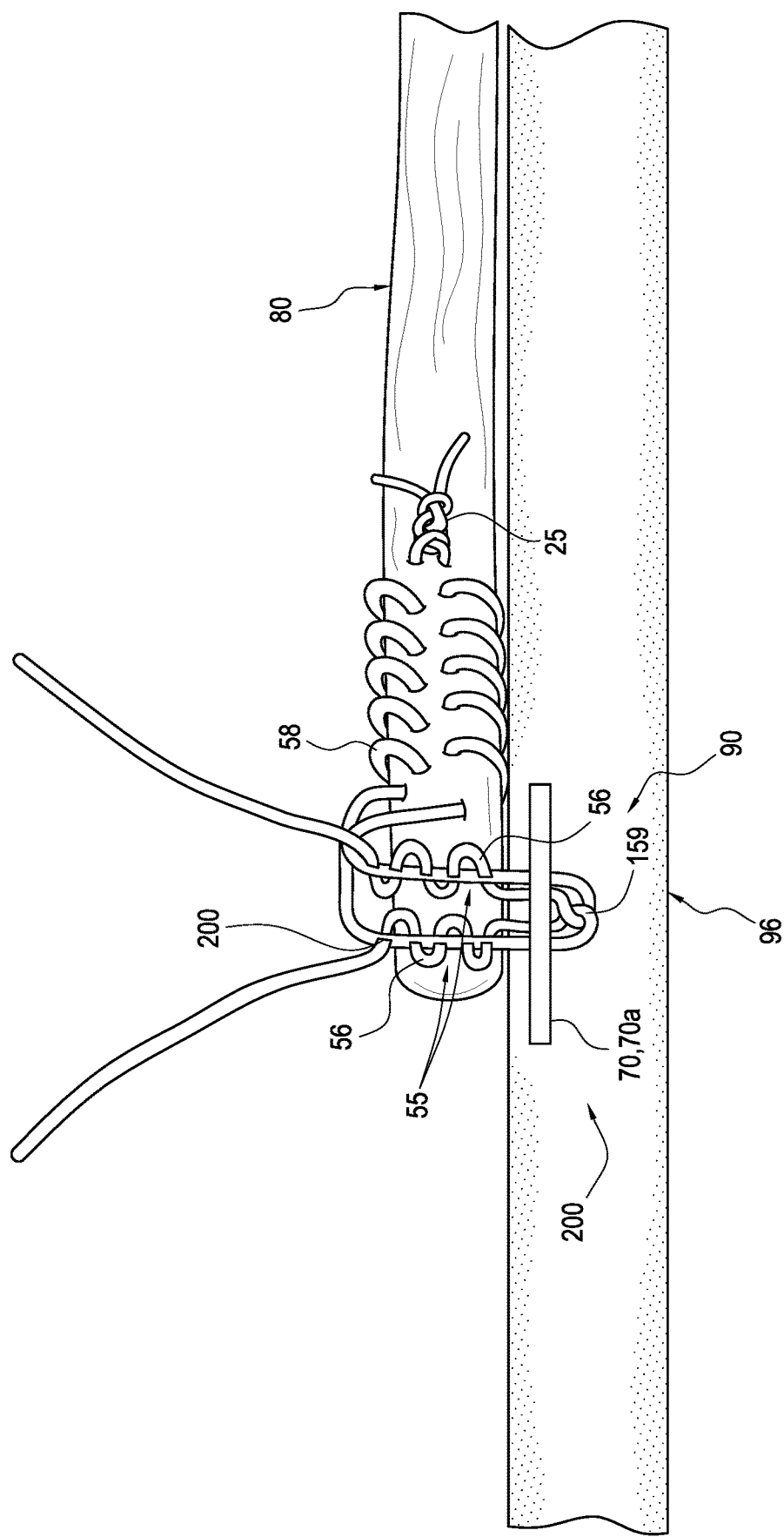
FIG. 10 illustrates the surgical construct of FIG. 6 with the inserter removed and the surgical construct attached to tissue.

FIG. 10 illustrates exemplary surgical construct 200 of FIG. 6 with the inserter 210 removed and attached to first and second tissue 80, 90. Surgical construct 200 is a self-locking suture button construct. The at least two flexible couplers 10, 20 of either round or flat design are run through implantable button 70, which may be a cortical button 70 secured to second tissue 90 (bone 90). The button 70 is inserted in bone 90 either uni-cortically or bi-cortically.

The at least two flexible couplers 10, 20 are passed through one another and through the holes of the cortical button 70 creating at least two flexible, adjustable, closed, knotless loops 50 having adjustable perimeters. One terminal end of each loop (ends 1 and 2) is run back through the suture 10, 20 in an accordion/pleat weave 55 and/or Chinese trap fashion to complete the loop(s), and create friction locking points 56. The other terminal ends (3 and 4) of the flexible coupler 10, 20 in which ends 1 and 2 are woven through, are used to stitch and secure a first tissue 80 (a tendon, ligament, and/or soft tissue). Tension is then applied to ends 1 and 2 to shrink/close the loops 50 bringing the button 70 and first tissue 80 (tendon/ligament/and/or soft tissue) and ends 3 and 4 of the couplers together, while locking the construct in place. Ends 3 and 4 may be tied in a knot 25 adjacent locking whipstitch area 58.

Figure 12:
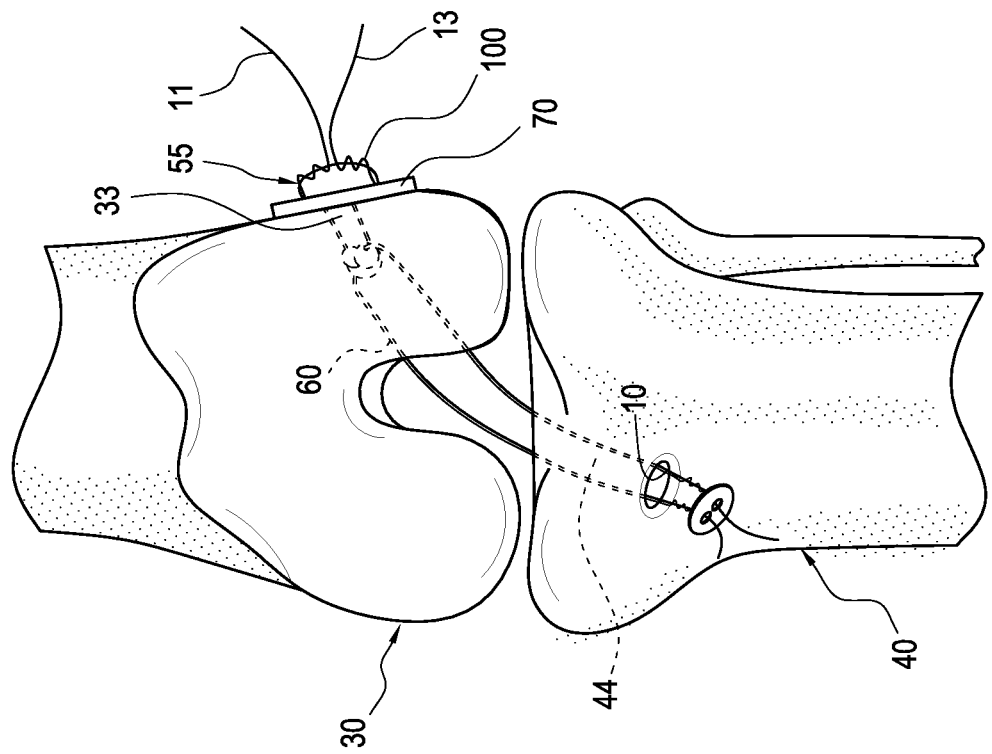
FIG. 12 illustrates the surgical construct of FIG. 11 employed in ACL reconstruction.
Figure 11:
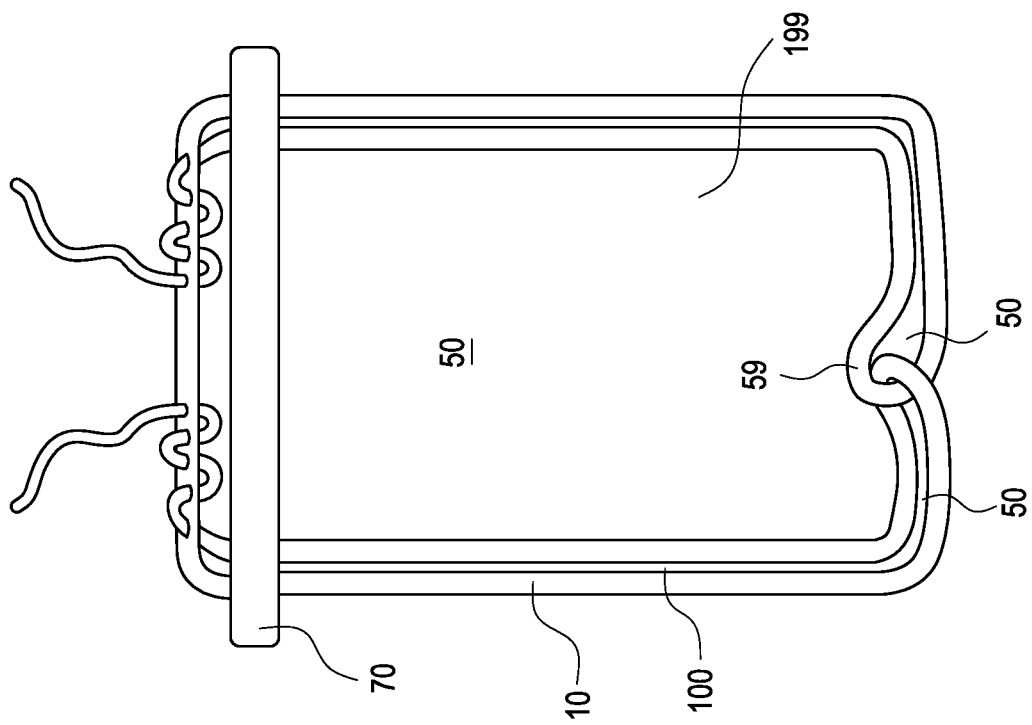
FIG. 11 illustrates a surgical construct according to an exemplary embodiment.

FIGS. 11 and 12 illustrate another view of the surgical construct 100 of FIG. 9 with self-locking tensionable construct 199 attached to only one fixation device (for example, cortical button 70) and employed in an exemplary ACL reconstruction. FIG. 12 illustrates surgical construct 100 with self-locking tensionable construct 199 attached to fixation device 70 and with graft 60 looped over interconnection 59. Graft 60 may be an ACL or PCL graft, for example. Surgical construct 100 attaches first tissue (for example, graft 60) to a second tissue (for example, femur 30). Surgical construct 100 extends within a femoral tunnel 33 formed within femur 30 and allows graft 60 to be passed through loop 50 and over loop interconnection 59 of the construct and be further secured within a tibial tunnel or socket 44 formed within tibia 40. Fixation device 70 may be a cortical button that may be passed through femoral tunnel 33 and exits the femoral cortex to rest upon it, as shown in FIG. 12.

FIGS. 13-15 illustrate self-locking tensionable construct 99, 199 attached to two fixation devices 70 to form surgical constructs 100a, 100b, 100c. Surgical construct 100a is formed of a continuous, single, flexible coupler 10 connected/looped through two fixation devices (for example, two buttons 70) to form at least two continuous, flexible, knotless, closed, adjustable loops 50 connected by an interconnect 59, and two accordion pleat self-locking suture weave regions 55 located on outer surface of button 70 (i.e., the surface facing away from the flexible loops 50).

FIG. 14 illustrates surgical construct 100b which is about similar to surgical construct 100a of FIG. 13, but differs from it in that the flexible coupler does not form interconnection 59, and the two accordion pleat self-locking suture weave regions 55 are located on inner surface of button 70 (i.e., the surface facing the flexible loops 50) as opposed to the outer surface. FIG. 15 is an enlarged view of the coupling tails of another surgical construct 100c, which is about similar to surgical construct 100b of FIG. 14, but differs in that the tails 11, 13 are passed through the passages of the fixation devices 70 after the formation of the accordion pleat selflocking suture weave regions 55.

Surgical constructs 100, 100a, 100b, 100c, 200, 200a, 300, 300a create knotless self-locking repairs. A self-locking suture button implant is provided for self-locking soft tissue repairs, for example, for self-locking tendon reattachment. A self-locking device incorporating a locking mechanism (accordion pleat-weave tape suture locking mechanism) to lock flexible strands, particularly suture tapes, is also disclosed. The locking mechanism may be employed with any suture tape, i.e. SutureTape, LabralTape, FiberTape®, etc. and allows self-locking devices to be formed out of suture tape rather than conventional suture or round suture such as FiberWire® suture.

The self-locking suture button implant and the self-locking mechanism (accordion pleat-weave tape suture locking mechanism) may be utilized to attach soft tissue (tendon) to bone such as in shoulder repair or fixate a graft in ACL or PCL reconstruction, for example, in a self-locking manner. The self-locking suture button implant and the self-locking mechanism (accordion pleat-weave tape suture locking mechanism) may be utilized in surgical procedures such as rotator cuff repair, Achilles tendon repair, patellar tendon repair, ACL/PCL reconstruction, hip and shoulder reconstruction procedures, AC joint reconstruction, syndesmosis reconstruction, quad/patellar tendon rupture repair, hallux-valgus repair, biceps tendon repair, humerus and radius repair, and any other tendon repair to bone, among many others, all conducted in a self-locking manner.

Figure 16:
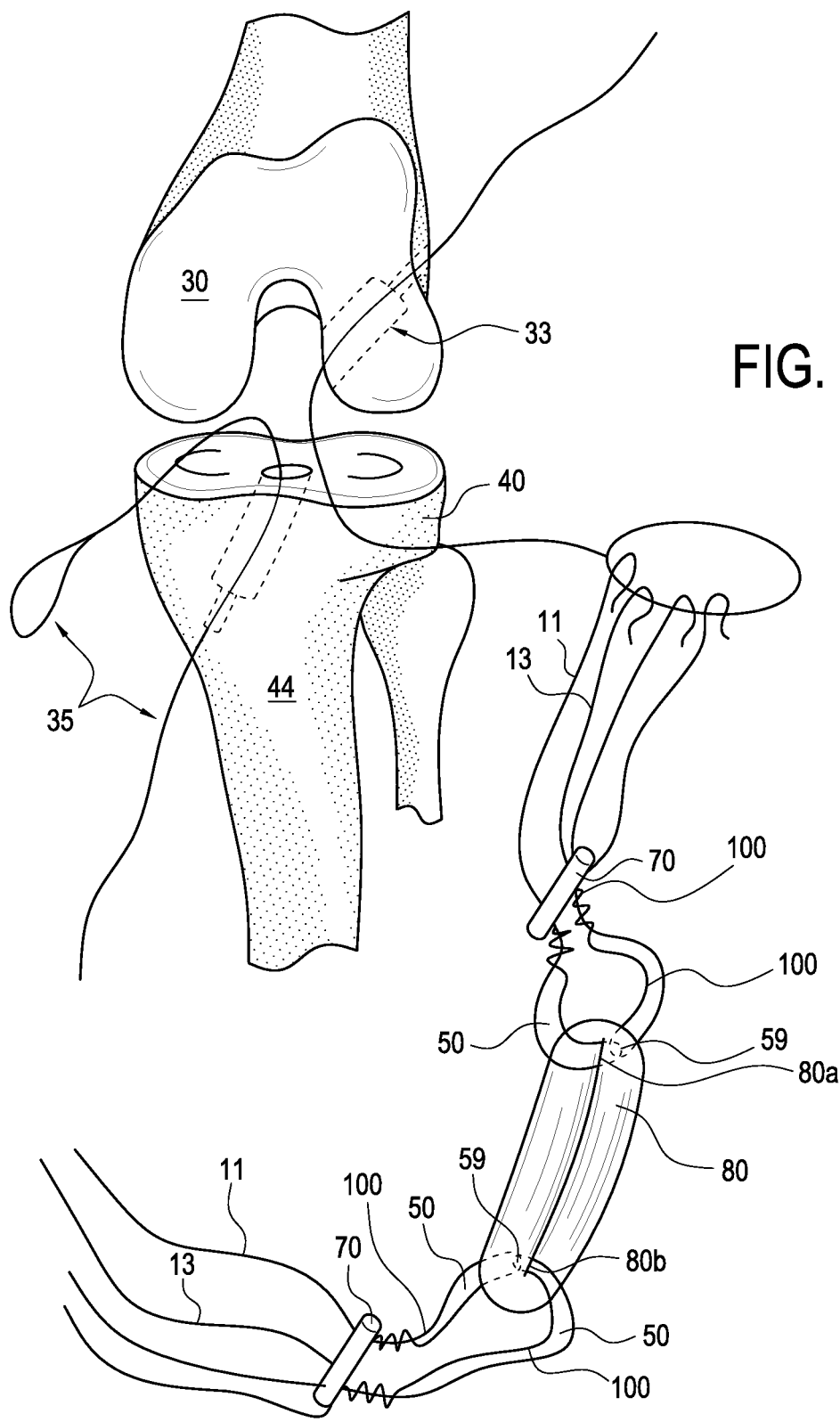
FIGS. 16-18 illustrate subsequent steps of an exemplary method of tissue repair (ACL reconstruction) with surgical constructs.
Figure 17:
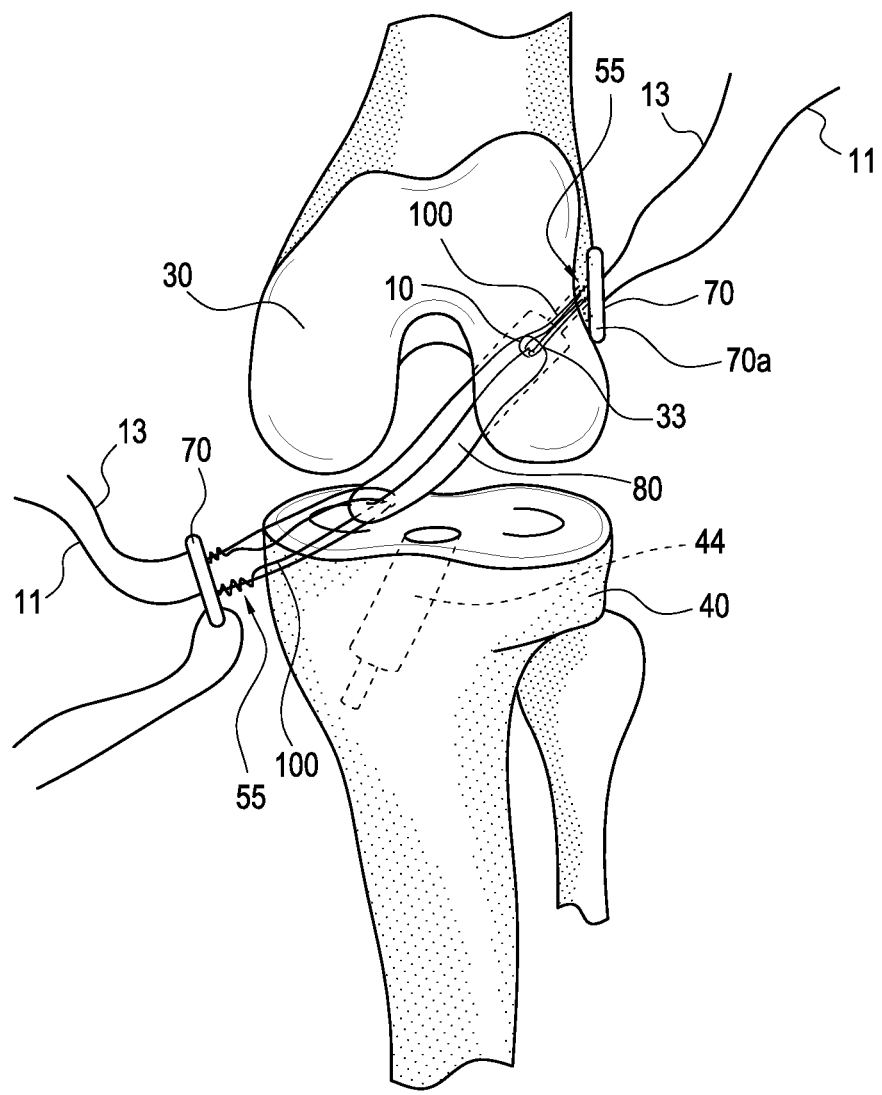
Figure 18:
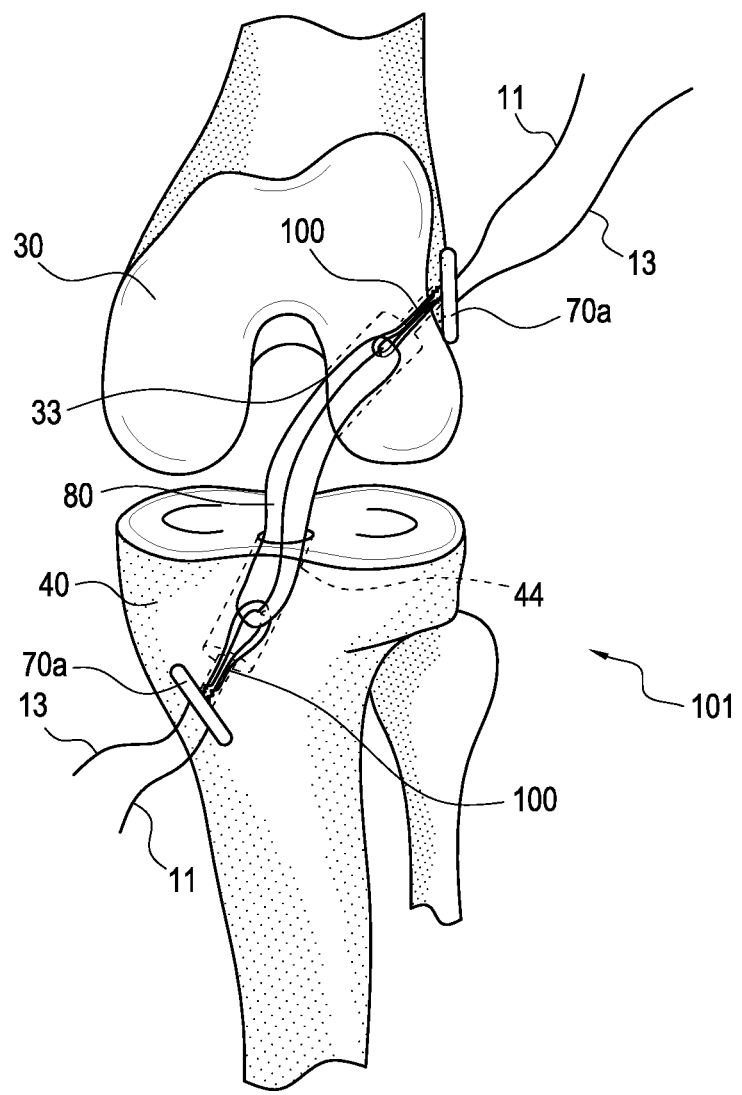

FIGS. 16-18 illustrate an exemplary ACL graft reconstruction with self-locking surgical constructs of the present disclosure. FIG. 16 illustrates tissue 80 (with stitched ends 80a, 80b) looped directly over interconnections 59 of the two flexible couplers 10 of two surgical constructs 100 employed in a method of ACL reconstruction according to an exemplary embodiment of the disclosure. Terminal ends 11, 13 of each flexible coupler 10 are used to control and adjust the length of the knotless, self-locking, adjustable loops 50. In embodiments without interconnection 59 (such as shown in FIGS. 3 and 7, for example), tissue 80 could be looped directly over the flexible couplers 10, 20.

The femoral socket 33 of femur 30 may be drilled transtibially, or through the medial portal, or by a retrograde technique. The femoral socket 33 is drilled in femur 30 to a depth about equal to the amount of graft desired in the femoral socket. After creating tibial tunnel 44 in tibia 40, a passing suture/shuttle suture 35 (FIG. 16) is brought through tibia 40 and out the femur 30. The first fixation device 70 (first button 70) is pulled through the femur 30 until it exits the lateral cortex to achieve fixation (FIG. 17). No tension should be put on the loop shortening strands until the button has been passed, self-flips, and is fully seated against the femoral cortex, as this could compromise graft advancement.

The graft is advanced and tension is pulled on the terminal ends 11, 13. The terminal ends may form a knot and/or may be cut with a cutting instrument such as an arthroscopic cutter. The technique proceeds with tibial fixation with second fixation device 70 (second button 70). FIG. 18 illustrates repair 101 with graft 80 completely seated in the femoral and tibial sockets/tunnels. The construct 100 is also ideal for all-inside ACL reconstruction. The adjustability of the implant simplifies graft length determination and allows graft tensioning from the femoral side.

Figure 19:
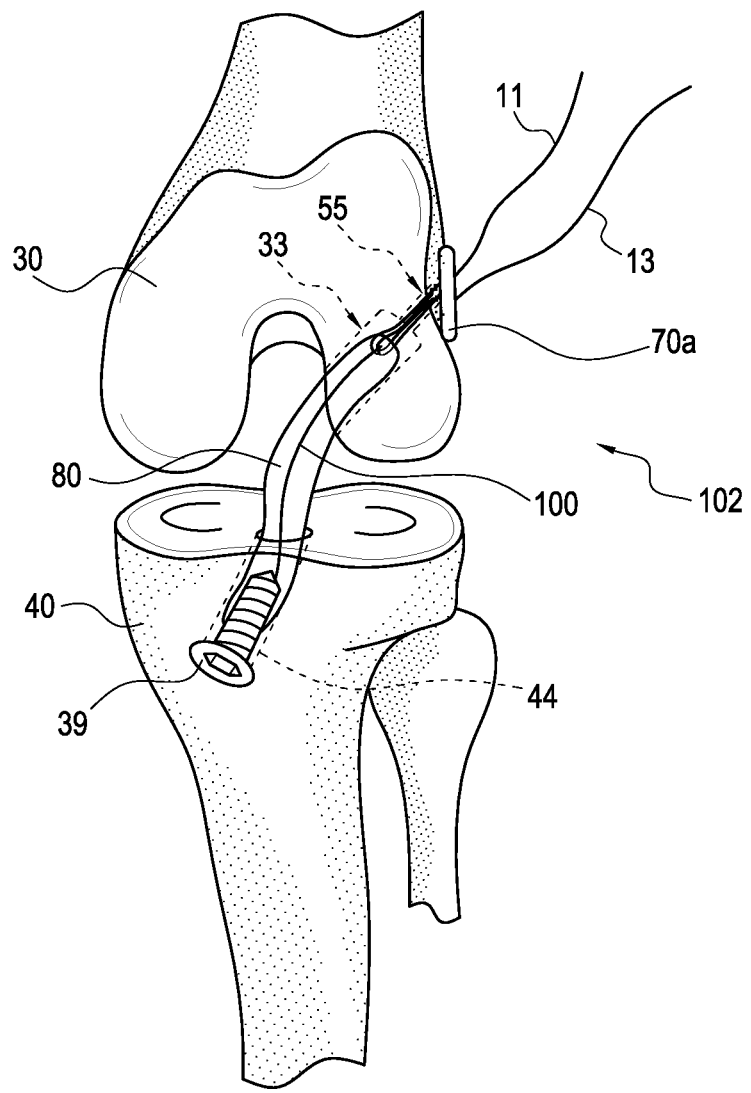
FIG. 19 illustrates another exemplary method of tissue repair (ACL reconstruction) with surgical constructs.

FIG. 19 illustrates a self-locking ACL repair 102 with tissue (graft) 80 secured within femoral socket 33 and tibia socket 44 by adjustable construct 100 and an interference device 39 (for example, an interference screw 39) in lieu of another self-locking construct (such as another construct 100).

The adjustable loop of the self-locking tensionable construct 99, 199 is adjustable under tension when the surgeon simply pulls on both terminal ends of the final construct 100 to adjust the length of the flexible loop and to tighten, therefore, the construct. The button 70 is pulled out of the bone cortex with the passing sutures (which are later discarded) and self-flips onto the cortex immediately upon exiting.

The ACL reconstructions detailed above offer adjustable cortical fixation for cruciate ligament reconstruction in a self-locking manner. The self-locking mechanism of the knotless construct 100 resists cyclic displacement and offers maximum loads equal to closed loop devices. The present disclosure eliminates the need for multiple sized loops and facilitates complete graft fill of short femoral sockets that are common with anatomic ACL drilling.

The ACL reconstruction construct above preferably includes a suture tape such as an ACL TapeRope. The device is used to reattach soft tissue to bone, bone to bone, ligament and/or tendon to bone. The device includes a flat tape (suture tape) run through one or two cortical buttons. One continuous loop is threaded through both buttons and interwoven back through itself in an accordion/pleat weave fashion to make a self-locking adjustable loop construct. The device may be provided assembled, disassembled, with or without buttons, to facilitate passing through a bone plug, and/or being passed prior to attachment of button(s).

Although the embodiments above have been described with reference to particular. ACL reconstruction techniques, the disclosure is not limited to these exemplary embodiments. Accordingly, the present disclosure also contemplates embodiments wherein a self-locking suture button implant and novel self-locking mechanism of the present disclosure is employed for additional tissue positioning and/or tissue adjustment applications, for example, in fixation of bone to bone (such as small joint applications, or acromioclavicular joint fixation techniques) which employ two fixation devices (for example, two buttons) joined by a continuous suture loop formed by a continuous flexible coupler. In these applications, a second fixation device (for example, a second button) is used in conjunction with the first button and with the flexible coupler, and with the accordion-style weave region between the two buttons, to complete the self-locking repair.

In exemplary embodiments only, the self-locking tensionable construct 99, 199 of the present disclosure may be employed in a method of bunion repair as described in U.S. Pat. No. 7,875,058 issued Jan. 25, 2011, and/or in a method of Lisfranc repair as described in U.S. Pat. No. 7,901,431 issued Mar. 8, 2011, the disclosures of both of which are incorporated by reference in their entirety herewith (wherein the flexible coupler of self-locking tensionable construct 99, 199 would be attached to first and second buttons). Similarly, the self-locking tensionable construct 99, 199 of the present disclosure may be employed in a method of fixation of bone to bone as described in U.S. Pat. No. 9,005,245 issued Apr. 14, 2015, the disclosure of which is incorporated by reference in its entirety herewith (wherein the flexible coupler of self-locking tensionable construct 99, 199 would be attached to first and second buttons, so that the flexible coupler extends between a plurality of bone tunnels and secures at least a first bone to a second bone in a self-locking manner).

Figure 20:
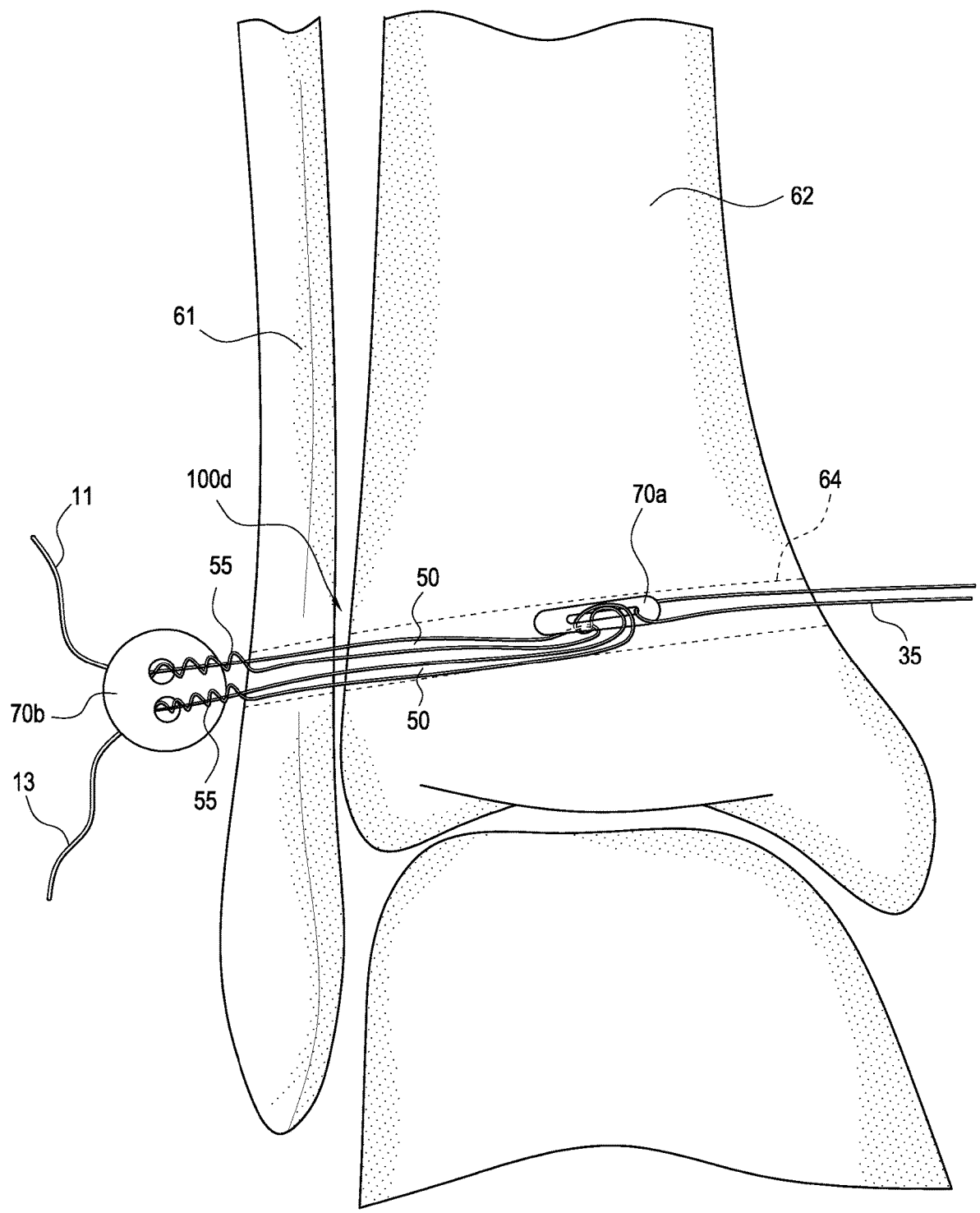
FIGS. 20 and 21 illustrate subsequent steps of an exemplary method of tissue repair (syndesmosis) with surgical constructs.
Figure 21:
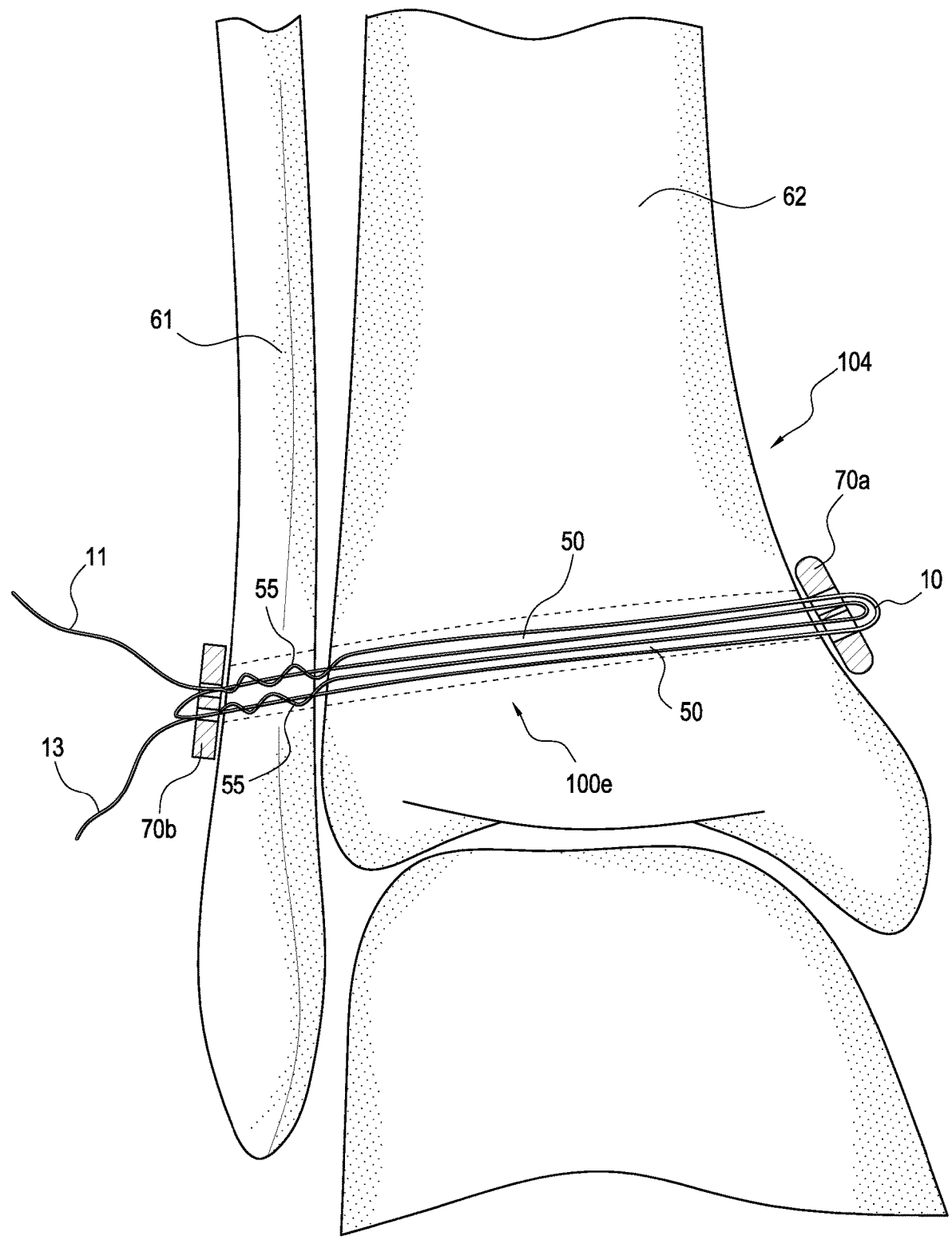

FIGS. 20 and 21 illustrate an exemplary method of ankle syndesmosis self-locking repair with construct 100*d*, 100*e* formed of self-locking tensionable construct 99, 199 with a flexible coupler 10 attached to different fixation devices 70*a*, 70*b* (for example, two buttons with a round and rectangular configuration, respectively). Construct 100*d* is secured within the fibula 61 and tibia 62 of an ankle joint. The method includes the steps of drilling a hole 64 through fibula 61 and tibia 62; pulling a first button 70*a* through the hole 64 using a pull-through suture 35 and/or being pushed through on an inserter until the first button 70*a* exits on a medial side of the tibia 62; flipping the first button 70*a* so it rests against a medial cortex of the tibia 62; and positioning a second button 70*b* together with the weave pleat accordion-style region 55 at a lateral side of the fibula 61.

Construct 100*d* is a syndesmotic TapeRope which is employed to repair the ankle syndesmosis. The device includes two cortical buttons 70*a*, 70*b* connected by a continuous flat/tape flexible coupling 10 that is woven through itself in an accordion/pleat fashion to create a self-locking mechanism 55 as part of self-locking tensionable construct 99, 199. The two terminal ends 11, 13 of the flexible coupling 10 are pulled to collapse the continuous loop 50, bringing buttons 70*a*, 70*b* closer together. After appropriate tension is achieved, both ends 11, 13 are cut flush to the button 70*b*.

Construct 100*e* of FIG. 21 is similar to construct 100*d* but differs in that final repair 104 of FIG. 21 includes the self-locking mechanism 55 (accordion weave regions 55) located within fibula 61 and not over the cortex, as in FIG. 20.

Figure 22:
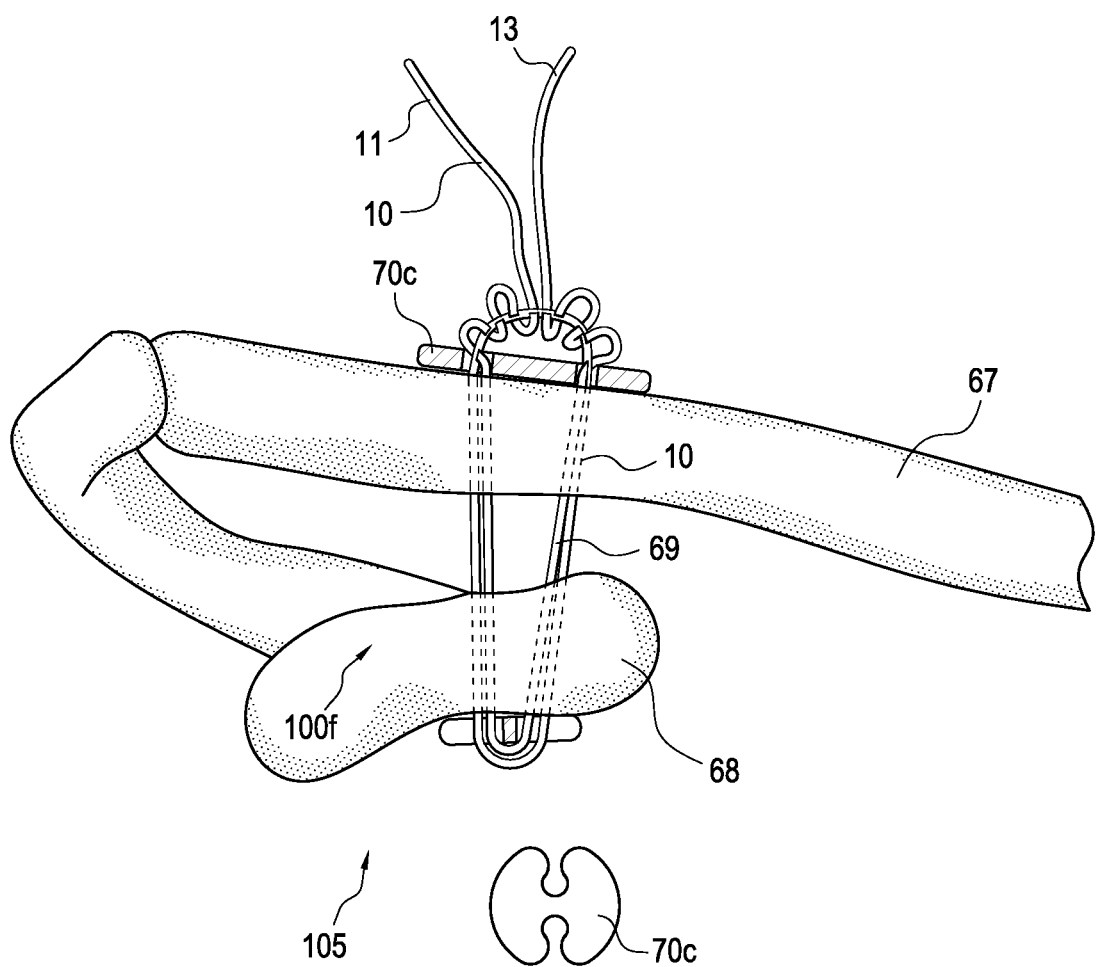
FIG. 22 illustrates an exemplary method of tissue repair (knotless AC repair) with surgical constructs.

FIG. 22 illustrates another exemplary method of tissue reconstruction with the constructs of the present disclosure. Knotless self-locking acromioclavicular (AC) joint fixation 105 is achieved with two fixation devices (for example, two buttons) connected by at least one continuous loop of a flexible coupler 10. Each button is provided with two or more openings to allow the passage of the flexible coupler. The flexible coupler 10 may be tape, for example, suture tape such as LabralTape or FiberTape® suture. The buttons may include a round button with a circular body and circular apertures (such as button 70*b*), an oblong button with an oblong body and with round or oblong apertures (such as button 70, 70*a*), and/or a dog-bone shaped button 70*c* such as described in U.S. Pat. No. 9,421,007 issued Aug. 23, 2016, the disclosure of which is incorporated in its entirety herewith.

The construct 100*f* of FIG. 22 used to repair AC joint separation includes two cortical buttons and one continuous flat/tape flexible coupling (suture tape). The continuous loop is run over two cortical buttons (attached and/or attachable such as the case of the dog-bone shaped button 70*c*). The terminal ends 11, 13 of the flat/tape flexible coupling 10 are woven back through the coupling in an accordion/pleat weave fashion creating a self-locking mechanism 55. Applied tension to both terminal ends will shrink the collapsible loop and self-lock the construct.

A hole 69 is drilled through both cortices of the clavicle 67 and through both cortices of the coracoid 68, directly below the drilled clavicle tunnel. A suture passing shuttle is fed down through both the clavicle and coracoid tunnels, then retrieved below the coracoid. The end of the flat/tape flexible coupling 10 without a cortical button, and together with both free terminal ends 11, 13, are shuttled up through the coracoid 68 and through the clavicle 67, then retrieved superiorly. An attachable button 70*c* is placed on the superior aspect of the tape/flat flexible coupling, inside the collapsible loop 50. With one cortical button 70*c* on the inferior aspect of the coracoid 68, and one cortical button 70*c* on the superior aspect of the clavicle 67, tension is applied to the two terminal ends 11, 13 of the flat/tape flexible coupling 10, shrinking the collapsible loop 50, reducing the AC joint. The accordion/pleat weave locking mechanism 55 self-locks, and then both ends 11, 13 of the flat/tape flexible coupling 10 may be cut flush with the clavicle cortical button 70*c* to complete repair 105.

Figure 23:
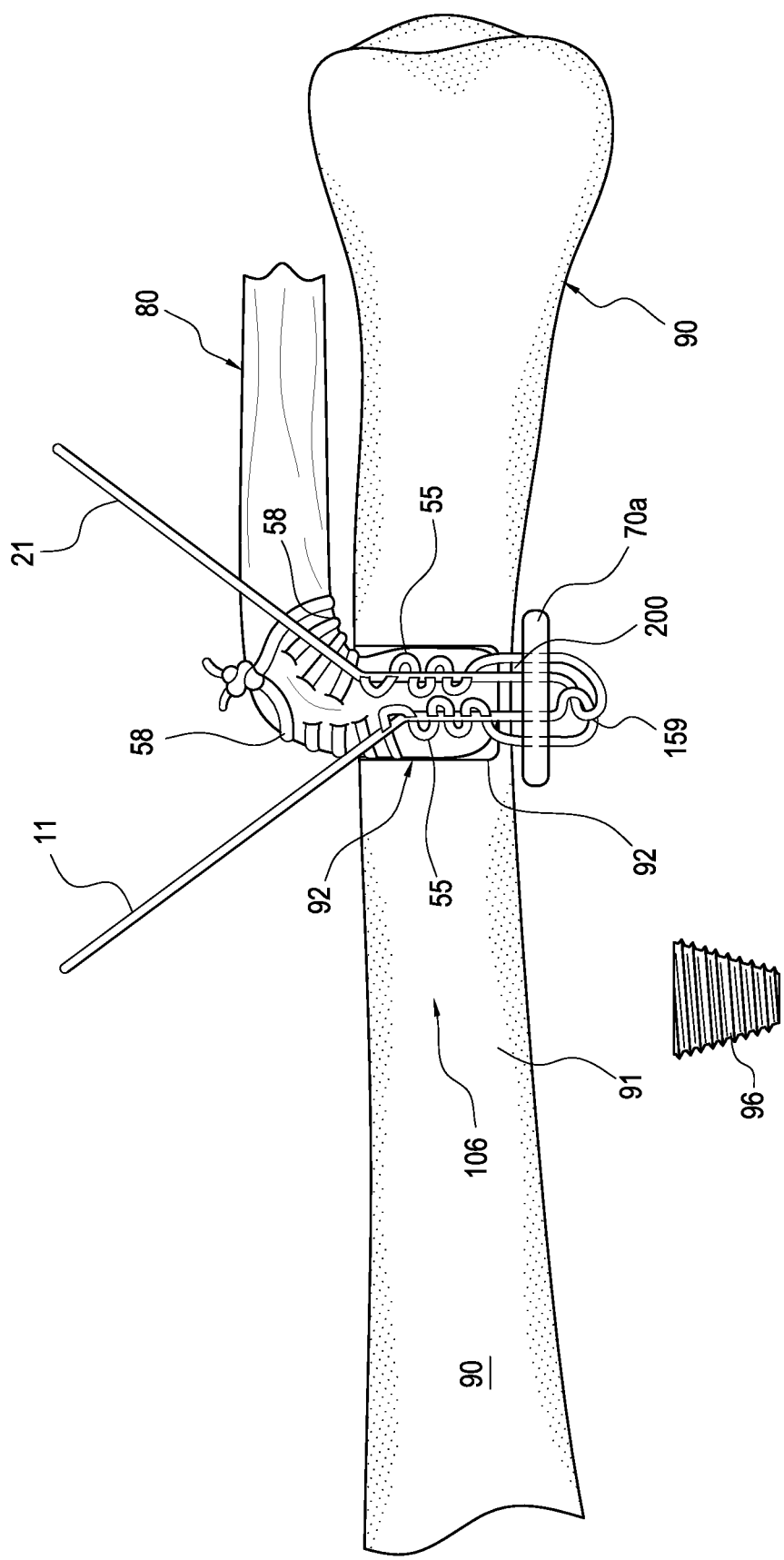
FIG. 23 illustrates an exemplary method of tissue repair (self-locking distal/proximal biceps repair) with surgical constructs.

FIG. 23 illustrates a self-locking distal/proximal biceps repair 106 with construct 200 of the present disclosure. Construct 200 approximates tendon 80 (biceps 80) to radius 91 and secures the tendon within a bone socket 92 formed within the radius 91. The flat tape suture tails 11, 21 are pulled to shrink the construct and bring the tendon 80 into the bone socket 92. The cortical button rests upon the bone cortex. The terminal ends 13, 23 of the flexible coupler 10, 20 are passed through the tendon 80 multiple times creating a plurality of locking stitches 58 (for example, locking whipstitches) on different regions of the tendon 80. Each accordion pleat weave self-locking mechanism/region. 55 is secured within the bone tunnel 92 and adjacent the tendon 80 and stitched regions 58. An optional interference screw 96 may be employed to provide additional reinforcement to the final repair 106.

Figure 24:
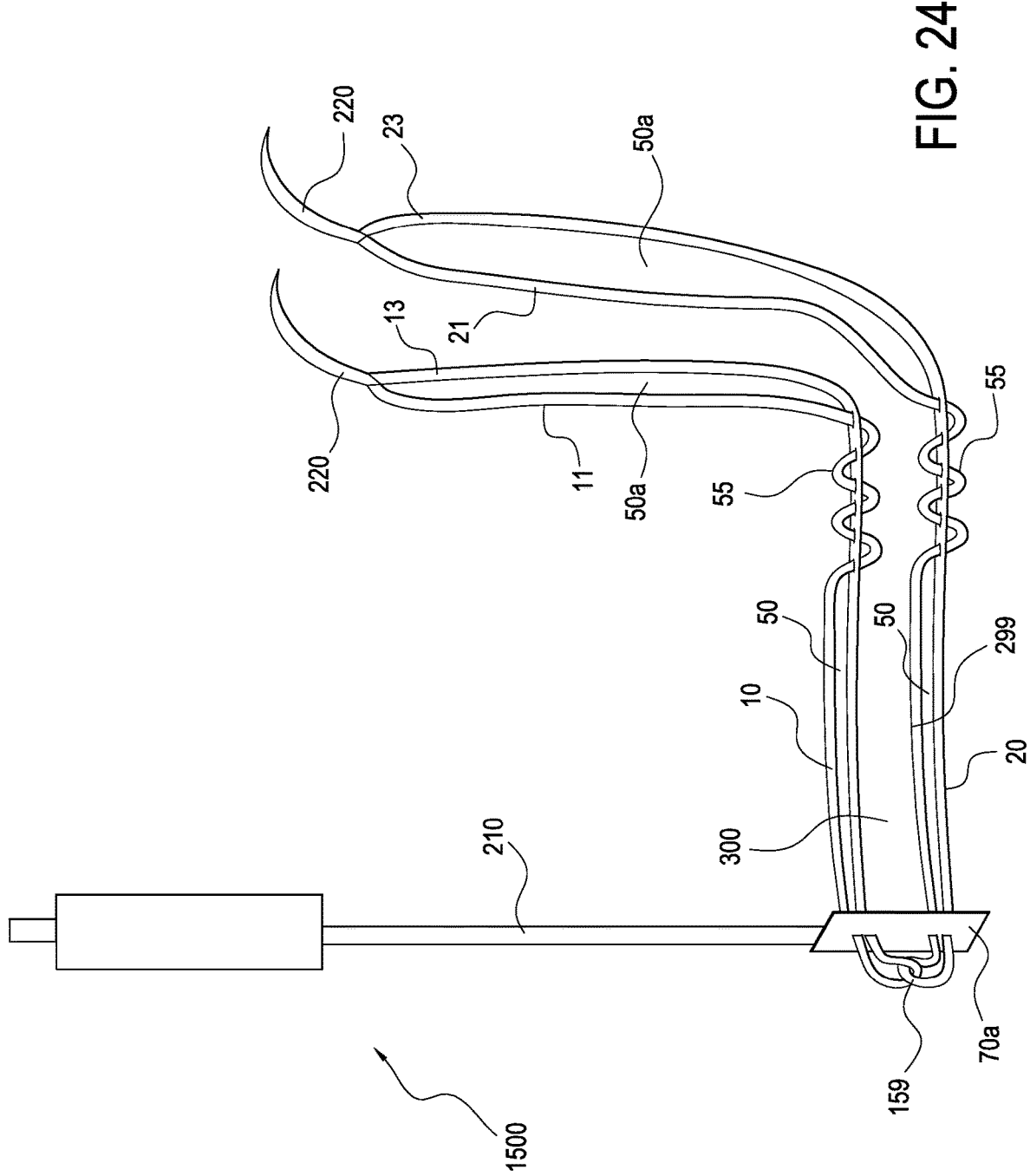
FIG. 24 illustrates a surgical assembly according to another exemplary embodiment.
Figure 25:
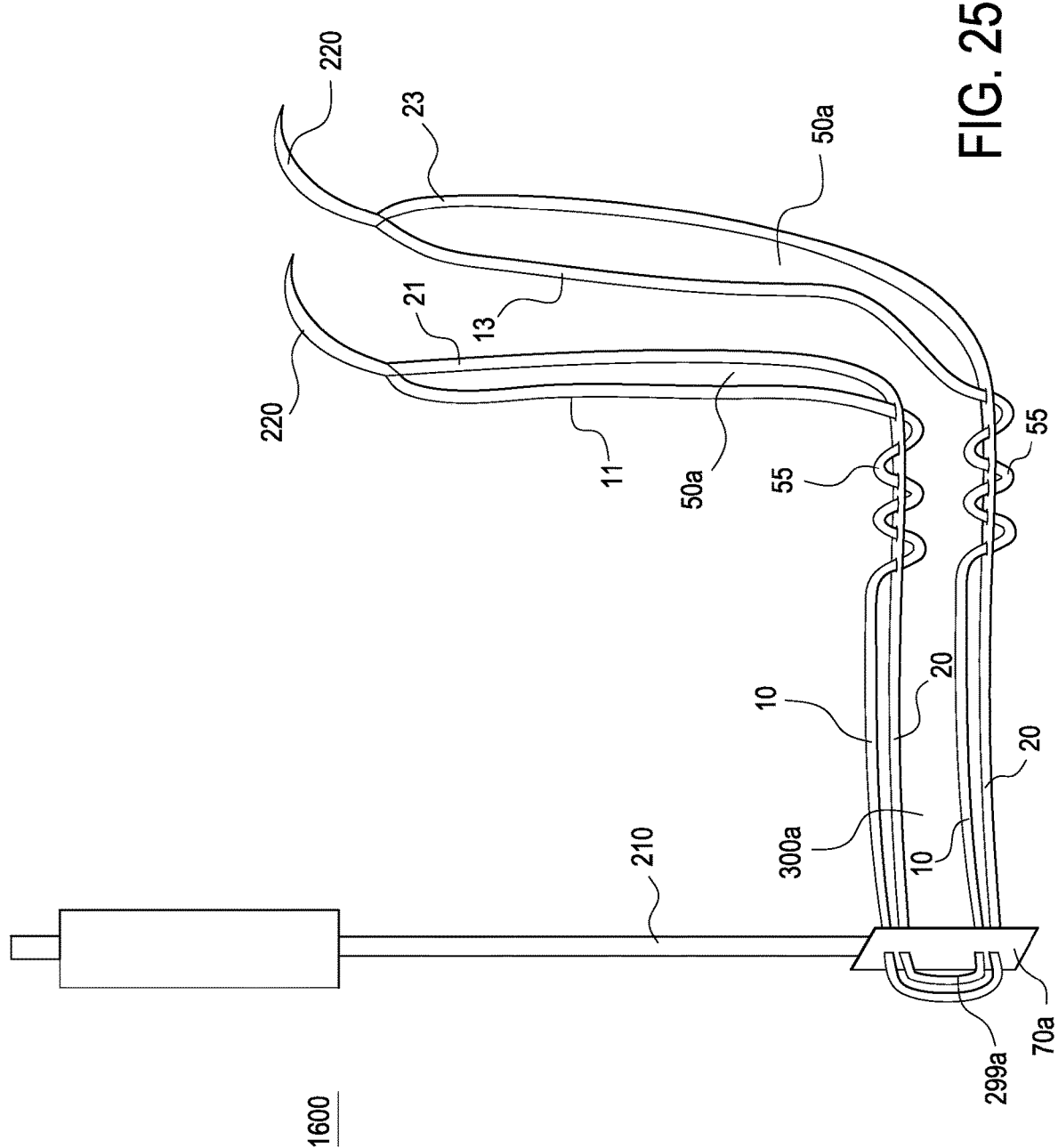
FIG. 25 illustrates a surgical assembly according to another exemplary embodiment.

FIGS. 24 and 25 illustrate surgical assemblies 1500, 1600 (surgical systems 1500, 1600) with inserter 210 pre-loaded with surgical constructs 300, 300a. Surgical constructs 300, 300 are similar in part with constructs 200, 200a of FIGS. 5-7 in that they also contain at least two flexible couplers 10, 20, each provided with terminal ends 11, 13 and 21, 23, respectively. The at least two flexible couplers 10, 20 also form at least two continuous, flexible, knotless, adjustable loops 50 and contain accordion style weave regions 55 that create multiple locking points 56 to lock the at least two suture loops 50. Surgical constructs 300, 300a differ from constructs 200, 200a in that the terminal ends 11, 13 and 21, 23, respectively, are each brought together (joined or coupled together) and are initially connected to a passing device 220 such as needle 220.

FIG. 24 illustrates surgical assembly 1500 (surgical system 1500) that includes inserter 210 attached to construct 300. Construct 300 includes at least two flexible couplers 10, 20 attached to a fixation device. The fixation device may be any one of fixation devices 70, 70a, 70c or any other fixation device, for example, an anchor, implant, screw, plate, etc. Both ends of each of the two flexible couplers 10, 20 are attached to a suturing/passing device 220 to allow passing of the flexible couplers 10, 20 through or around tissue 80. FIG. 24 illustrates exemplary ends 11, 13 of first flexible coupler 10 attached to exemplary needle 220, and exemplary ends 21, 23 of second flexible coupler 20 attached to another exemplary needle 220. The two exemplary suturing/passing devices 220 may be similar or different. Fixation device 70a may be a button or any similar structure that allows attachment to a flexible coupler and/or tissue to be fixated. In exemplary embodiments, fixation device 70a may be a button.

Attachment of the two terminal ends of each flexible coupler 10, 20 to suturing/passing device 220 allows formation of another flexible, adjustable, closed loop 50a, for each of the flexible coupler 10, 20, i.e., a first flexible, adjustable, closed loop 50a and a second flexible, adjustable, closed loop 50a. Each of the first and second flexible adjustable closed loops 50a is located between the suturing/passing device 220 and the respective weave region 55 having an accordion configuration. The two terminal ends may be brought together/coupled/joined by gluing, bonding, splicing, knotting, fusing, melting, heating, or by any other known method in the art. In certain embodiments, the connecting of the ends may be accomplished by splicing. The ends may be first joined together to form a single end and then the single end may be connected/attached to a suture passing device, such as needle 220. Alternatively, the two ends may be independently, separately and directly attached to a suture passing device, such as needle 220.

FIG. 25 illustrates surgical assembly 1600 (surgical system 1600) that includes inserter 210 attached to construct 300a. Construct 300a includes at least two flexible couplers 10, 20 attached to a fixation device. The fixation device may be any one of fixation devices 70, 70a, 70c or any other fixation device, for example, an anchor, implant, screw, plate, etc. Both ends of each of the at least two flexible couplers 10, 20 are attached to a suturing/passing device 220 to allow passing of the at least two flexible couplers 10, 20 through or around tissue 80. FIG. 25 illustrates exemplary ends 11, 13 of first flexible coupler 10 attached to exemplary needle 220, and exemplary ends 21, 23 of second flexible coupler 20 attached to another exemplary needle 220. The two exemplary suturing/passing devices 220 may be similar or different. Fixation device 70a may be a button or any similar structure that allows attachment to a flexible coupler and/or tissue to be fixated. In exemplary embodiments, fixation device 70a may be a button.

Attachment of the two terminal ends of each flexible coupler 10, 20 to suturing/passing device 220 allows formation of another flexible, adjustable, closed loop 50a, for each of the flexible coupler 10, 20, i.e., a first flexible, adjustable, closed loop 50a and a second flexible, adjustable, closed loop 50a. Each of the first and second flexible adjustable closed loops 50a is located between the suturing/passing device 220 and the respective weave region 55 having an accordion configuration. The two terminal ends may be brought together/coupled/joined by gluing, bonding, splicing, knotting, fusing, melting, heating, or by any other known method in the art. In certain embodiments, the connecting of the ends may be accomplished by splicing. The ends may be first joined together to form a single end and then the single end may be connected/attached to a suture passing device, such as needle 220. Alternatively, the two ends may be independently, separately and directly attached to a suture passing device, such as needle 220.

Fixation device 70a may be any device that allows passing of the flexible couplers therethrough (for example, through a plurality of openings or apertures or passages formed within a body of the fixation device) to form a plurality of continuous, knotless, self-locking, flexible, adjustable loops 50. In an exemplary embodiment, the fixation device is a cortical button having a slanted configuration that allows passage of the flexible couplers 10, 20 and formation of interconnection 159 (FIG. 24). Details of exemplary fixation device 70a have been provided above with reference to surgical constructs 200, 200a.

Subsequent to the passing of the at least two flexible couplers 10, 20 of surgical constructs 300, 300a through or around soft tissue (tendon), the flexible couplers are cut from the suturing/passing device 220 (needle 220) to allow further suturing of the tendon (for example, whipstitching of the tendon). Alternatively, the passing device (needle 220) is cut or removed from the construct.

Fixation device 70a may be any structure that allows passing of the flexible couplers 10, 20 therethrough to form the plurality of continuous, self-locking, flexible, knotless, adjustable loops 50. In an exemplary-only embodiment and as illustrated in FIG. 25, the fixation device is a cortical button having a slanted configuration that allows passage of the flexible couplers 10, 20 without formation of an interconnection.

The embodiments illustrated in FIGS. 24 and 25 have particular application to using the constructs in a unicortical procedure. Due to the thin cortical bone, if the surgeon does not pull the locking mechanism all the way up tight to the tendon when beginning the whip (Krackow) stitch, there is potential for a gap to be left between the locking mechanism and the tendon. This could result in poor compression at the tendon/bone interface. To alleviate this potential issue, both the tension sutures and whipstitch sutures are connected to the needles. Then, both sets of sutures are passed through the soft tissue (for example, tendon) on the first pass, bringing the locking mechanism through the tendon. Once this is done, only the tension suture is cut from the needles and the surgeon may proceed with the whip (Krackow) stitch. This simple step will ensure great compression at the tendon/bone interface, eliminating the potential for a gap that is too large being left between the locking mechanism and tendon. In an exemplary-only embodiment, the locking mechanism measures about 5 mm or less.

Figure 26:
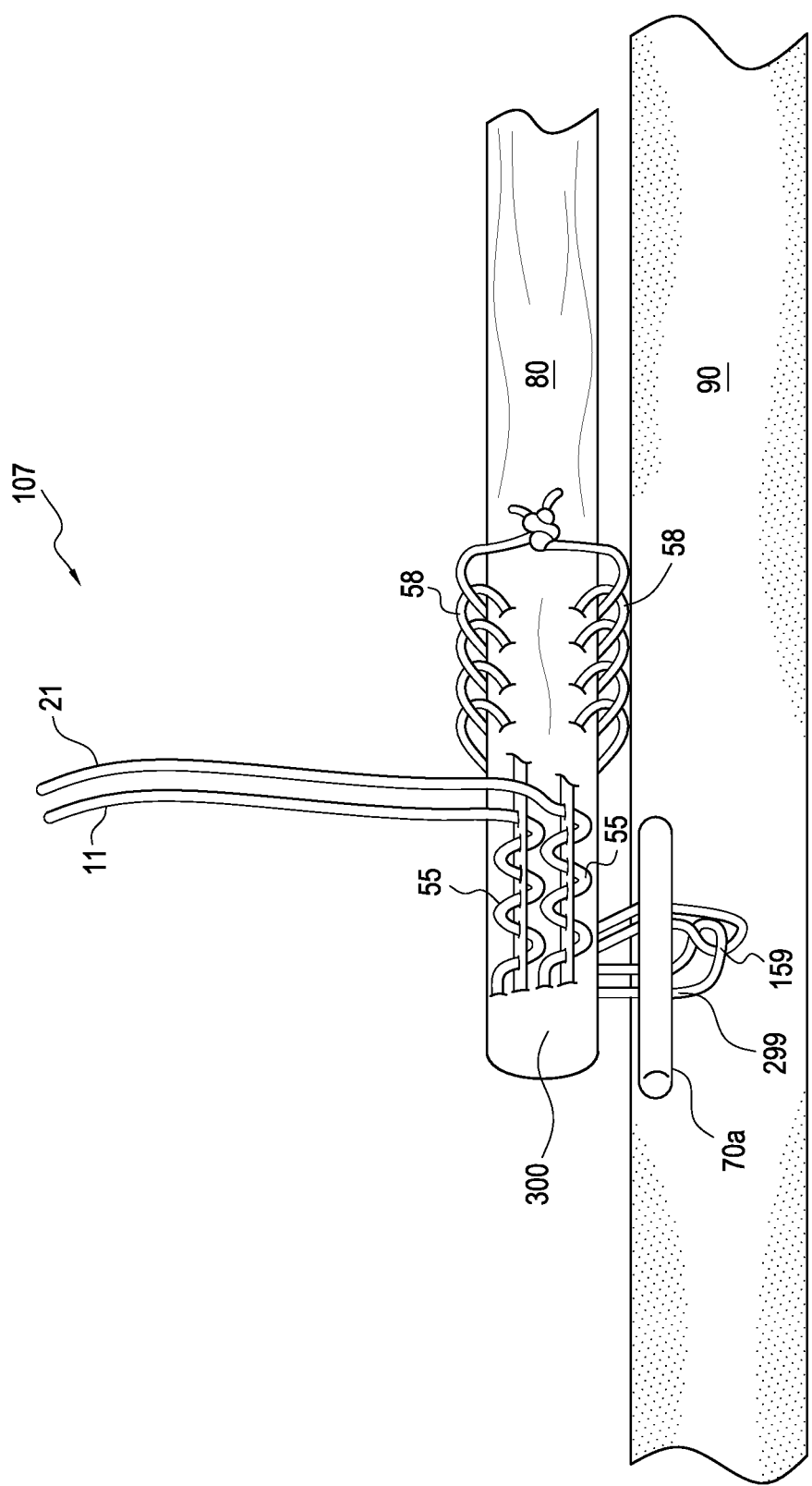
FIG. 26 illustrates an exemplary method of tissue repair with surgical constructs.

FIG. 26 illustrates exemplary surgical construct 300 of FIG. 24 with the inserter 210 removed and attached to first and second tissue 80, 90 to complete repair 107. Surgical construct 300 is a self-locking double-loaded suture button construct. The at least two flexible couplers 10, 20 of either round or flat design are run through exemplary implantable button 70a, which may be a cortical button 70a secured to second tissue 90 (bone 90). The button 70a is inserted in bone 90 either uni-cortically or bi-cortically.

The at least two flexible couplers 10, 20 are passed through one another and through the holes of the cortical button 70a creating at least two flexible, adjustable, closed, knotless loops 50 having adjustable perimeters. One terminal end of each loop is run back through the suture 10, 20 in an accordion/pleat weave 55 and/or Chinese trap fashion to complete the loop(s), and create friction locking points 56. The two ends of each of the two flexible couplers are then brought together/connected to needle 220 and passed through tendon 80. Needle 220 is removed and one end of each flexible coupler is used to stitch and secure a first tissue 80 (a tendon, ligament, and/or soft tissue). Tension is then applied to remaining ends to shrink/close the loops 50 bringing the button 70a and first tissue 80 (tendon/ligament/ and/or soft tissue) and remaining ends of the couplers together, while locking the construct in place. The remaining ends 11, 21 may be tied in a knot adjacent locking whipstitch area 58.

Surgical constructs and methods of knotless tissue repairs are disclosed. Any of self-locking tensionable construct 99, 199, 299, 299a and surgical constructs 100, 100a, 100b, 100c, 100d, 100e, 100f, 200, 200a, 300, 300a may be employed in the methods of self-locking repairs.

A knotless, adjustable, self-locking tensionable construct 99, 199, 299, 299a includes at least one flexible coupler 10 having a first end 11 and a second end 13; an optional loop interconnection 59 between the first end 11 and the second end 13; first and second closed, adjustable, continuous, flexible loops 50; and first and second weave regions 55 having an accordion configuration adjacent the first and second closed, adjustable, continuous, flexible loops 50 and adjacent the first and second ends 11, 13. A knotless, adjustable, self-locking construct may also include at least one fixation device 70 attached to the at least one flexible coupler 10.

A surgical construct comprises: a flexible coupler 10 passed through passages of a fixation device 70, 70a, 70c to form at least two flexible, adjustable, closed, knotless loops 50 with adjustable perimeters; an optional loop interconnection 59; two accordion-pleat weave regions 55 at a distance apart from the loop interconnection 59; and two terminal ends 11, 13. The flexible coupler 10 may be a suture tape and the fixation device 70, 70a, 70c may be an implantable button. The flexible coupler 10 may connect a first tissue 30 to a second tissue 60. The first tissue may be bone 30 and the second tissue may be soft tissue 60. Soft tissue 60 may be attached to the loop interconnection 59 and bone 30 may be attached to the fixation device 70, 70a, 70c. The flexible coupler may be passed through a second fixation device.

A surgical construct comprises: two flexible couplers 10, 20 passed through passages of a fixation device 70, 70a, 70c to form at least two flexible, adjustable, closed, knotless loops 50 with adjustable perimeters; an optional loop interconnection 159; two accordion-pleat weave regions 55 at a distance apart from the loop interconnection 159; and four terminal ends 11, 13, 21, 23. The flexible coupler 10, 20 may be a suture tape and the fixation device 70, 70a, 70c may be an implantable button. The flexible coupler 10, 20 may connect a first tissue to a second tissue. The first tissue may be bone 90 and the second tissue may be soft tissue 80. Two terminal ends 11, 21 of the flexible coupler 10, 20 are passed through the soft tissue 80 to form two or more stitched regions. The remaining terminal ends 13, 23 are pulled to decrease the distance between the fixation device and the soft tissue and decrease the length and perimeter of the flexible, adjustable, closed, knotless loops 50.

The two terminal ends of each of the flexible couplers 10, 20 may be brought together and attached to a suture passing device, such as needle 220. In certain embodiments, only two ends of one of the flexible couplers may be brought together and connected/attached to a suture passing device, such as needle 220, whereas the other two ends of the other flexible coupler may not be connected (or only one of the ends of the other flexible coupler may be attached to a suture passing device, such as needle 220).

A surgical assembly comprises: at least two flexible couplers 10, 20 passed through passages of a fixation device 70, 70a, 70c to form at least two flexible, adjustable, closed, knotless loops 50 with adjustable perimeters; at least two accordion-pleat weave regions 55; and at least four terminal ends 11, 13, 21, 23. The at least two flexible couplers 10, 20 may be sutures and/or suture tapes and the fixation device 70, 70a, 70c may be an implantable button. The at least two flexible couplers 10, 20 may connect a first tissue to a second tissue. The first tissue may be bone 90 and the second tissue may be soft tissue 80. Two terminal ends 11, 21 of the at least two flexible coupler 10, 20 are passed through the soft tissue 80 to form two or more stitched regions. The remaining terminal ends 13, 23 are pulled to decrease the distance between the fixation device and the soft tissue and decrease the length and perimeter of the flexible, adjustable, closed, knotless loops 50. The at least two flexible couplers 10, 20 may form interconnection 159.

In alternative embodiments, all terminal ends from one of the at least two flexible couplers 10, 20 may be joined/coupled together to a suture passing device (for example, needle). In alternative embodiments, all terminal ends from each of the at least two flexible couplers 10, 20 may be joined/coupled together to a separate suture passing device (for example, needle). In alternative embodiments, all terminal ends from each of the at east two flexible couplers 10, 20 may be joined/coupled together to a same suture passing device (for example, needle). The terminal ends may be coupled/joined together by gluing, bonding, knotting, fusing, melting, heating, splicing or by any other known method in the art. In certain embodiments, the connecting of the ends may be accomplished by splicing.

A method of tissue repair comprises inter alia: passing a flexible coupler 10 through passages 71 of a fixation device 70, 70a, 70c; passing each terminal end 11, 13 of the flexible coupler 10 through the flexible coupler multiple times to each form an accordion/pleat weave region 55 and a plurality of locking points 56, and at least two flexible, knotless, continuous, closed adjustable loops 55 with an adjustable perimeter and an optional loop interconnection 59; attaching a first tissue 60 to the loop interconnection and/or to the flexible coupler; securing the fixation device 70, 70a, 70c to a second tissue (for example, bone); and pulling on the terminal ends to lock the flexible coupler 10. The method may also include the steps of: securing the fixation device 70, 70a, 70c to an inserter 210.

A method of tissue repair comprises inter alia the steps of: passing a first flexible coupler 10 and a second flexible coupler 20 through passages 71 of a fixation device 70, 70a, 70c each of the first flexible coupler and the second flexible coupler having a first terminal end 11, 21 and a second terminal end 13, 23; interconnecting the first flexible coupler with the second flexible coupler to form an interconnection 159; passing one terminal end from each of the first and second flexible couplers through respective flexible coupler to form a first friction locking weave region 55 and a second friction locking weave region 55; passing the other terminal ends of the first and second flexible couplers through soft tissue 80 to form first and second stitched regions 58; and pulling on the terminal ends from the first and second friction locking weave regions 55 to reduce the distance between the fixation device 70, 70a, 70c and the soft tissue 80. The method may be also conducted without interconnecting the first and second flexible couplers to form interconnection 159, i.e., by running the first and second flexible couplers in parallel to each other, as shovai in FIG. 7, for example.

The self-locking tensionable construct 99, 199, 299, 299a and surgical construct 100, 100a, 100b, 100c, 100d, 100e, 100f, 200, 200a, 300, 300a of the present disclosure has applicability to surgical procedures such as rotator cuff repair, Achilles tendon repair, patellar tendon repair, ACL/PCL reconstruction, hip and shoulder reconstruction procedures, proximal and/or distal biceps repairs, and any tissue to tissue repair applications.

Tensionable construct 99, 199, 299, 299a may be formed of flexible couplers that are flexible materials and strands such as flat suture, ribbons or flat tape (for example, suture tape) or combination of suture and tape. The flexible strands/couplers may have cross-sections of various forms and geometries, including round, oval, rectangular, or flat, among others, or combination of such forms and geometries. In an exemplary embodiment only, at least one of the at least two flexible couplers 10, 20 may be suture such as Fiber-Wire® suture or flat suture tape that is braided, knitted or woven.

The flexible couplers may include any flexible materials or strands such as suture or tape, for example, multifilament, braided, knitted, woven suture, or including fibers of ultra-high molecular weight polyethylene (UHMWPE) such as FiberWire® suture. The flexible couplers may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical self-locking constructs can be used with any type of flexible material or suture known in the art. If suture tape is employed, the tape may have sections with different tapers (for example, 3 or 4 sections of gradual tapers or gradual widths) to facilitate easy formation of the accordion style weave regions 55.

The flexible couplers 10, 20 may be also formed of a stiff material, or combination of stiff and flexible materials, particularly for the regions of the couplers that are weaved through the body of the coupler and depending on whether they are employed with additional fixation devices. In addition, flexible couplers may be also coated and/or provided in different colors for easy manipulation during the surgical procedure. The knotless constructs and self-locking soft anchors of the present disclosure can be used with any type of flexible material or suture that may be weaved or passed through itself.

Surgical construct 100, 100a, 100b, 100c, 100d, 100e, 100f, 200, 200a, 300, 300a may be also coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture or tape, knot security, pliability, handleability or abrasion resistance, for example. If desired, at least one of the flexible couplers 10, 20 may be coated, impregnated, or otherwise stiffened with a material such as plastic, for example.

The flexible couplers 10, 20 of the surgical construct 100, 100a, 100b, 100c, 100d, 100e, 100f, 200, 200a, 300, 300a may be also provided with tinted tracing strands, or otherwise contrast visually with the sheath of the construct, which remains a plain, solid color, or displays a different tracing pattern, for example. Various structural elements of surgical construct 100, 100a, 100b, 100c, 100d, 100e, 1100f, 200, 200a, 300, 300a may be visually coded, making identification and handling of the suture legs simpler. Easy identification of suture in situ is advantageous in surgical procedures, particularly during arthroscopic surgeries, such as endoscopy and laparoscopy.

The disclosure provides a self-locking tensionable construct, comprising: a flexible coupler having a first end and a second end; a loop interconnection between the first end and the second end; first and second closed, adjustable, continuous, flexible loops; and first and second weave regions having an accordion configuration adjacent the first and second closed, adjustable, continuous, flexible loops and adjacent the first and second ends. Each of the first and second closed, adjustable, continuous, flexible loops is located between one of the first and second ends and the loop interconnection. Each of the first and second weave regions is located between one of the first and second ends and one of the first and second closed, adjustable, continuous, flexible loops. The flexible coupler is suture, suture tape or ribbon. The flexible coupler is a suture tape with a plurality of sections of different tapers. The flexible coupler is a suture tape with three or four sections of gradual taper. The first and second ends are pulled to lock the tensionable construct. The tensionable construct consists essentially of the flexible coupler.

The disclosure also provides a surgical construct for tissue repair comprising: a self-locking tensionable construct extending between two fixation devices, the self-locking tensionable construct including a flexible coupler extending through bodies of the two fixation devices and forming at least two flexible, continuous, closed, adjustable, knotless loops; a loop interconnection; and two terminal ends, wherein each terminal end is passed multiple times through the flexible coupler to each form an accordion-type weave region and a plurality of locking points.

The accordion-type weave regions and plurality of locking points are located adjacent one of the two fixation devices, and the loop interconnection is located adjacent the other of the two fixation devices. The two fixation devices are two implantable buttons and the flexible coupler is a suture tape. Each terminal end is configured to be pulled to lock the surgical construct. Each terminal end is configured to be pulled to decrease a length and perimeter of the at least two flexible, continuous, closed, adjustable, knotless loops. The tissue repair is rotator cuff repair, AC joint repair, syndesmosis repair, Achilles tendon repair, patellar tendon repair, ACL/PCL reconstruction, hip and shoulder reconstruction, AC joint reconstruction, syndesmosis reconstruction, quad/patellar tendon rupture repair, or hallux-valgus repair.

The disclosure also provides a method of forming a knotless self-locking repair, comprising: attaching a first flexible coupler with a first end and a second end to a fixation device by passing one of the first and second ends through passages of the fixation device, wherein the other of the first and second ends is attached to a first passing device; passing the one of the first and second ends through the first flexible coupler multiple times to form a first accordion-type weave region and a plurality of locking points, and a first flexible, continuous, closed, adjustable, knotless loop; attaching a second flexible coupler with a first end and a second end to the fixation device by passing one of the first and second ends through the passages of the fixation device, wherein the other of the first and second ends is attached to a second passing device; and passing the one of the first and second ends through the second flexible coupler multiple times to form a second accordion-type weave region and a plurality of locking points, and a second flexible, continuous, closed, adjustable, knotless loop.

The first and second flexible, continuous, closed, adjustable, knotless loop are separated by a loop interconnection. The at least one of the first and second passing devices is a suturing device. The suturing device is a needle. The method further comprises the step of suturing soft tissue with at least one of the first and second passing devices and at least one of the first and second couplers.

The method further comprises cutting at least one of the first and second flexible couplers. The method further comprises the steps of: attaching a first tissue to the first and second couplers by passing the first and second passing devices through the first tissue; attaching the fixation device to a second tissue; pulling on the one of the first and second ends of each of the first and second couplers to adjust tension of the first and second flexible, continuous, closed, adjustable, knotless loops, to approximate the first tissue to the second tissue. The first tissue is soft tissue and the second tissue is bone.

Although the embodiments above have been described with reference to constructs formed of one or two flexible couplers such as flexible couplers 10, 20, the disclosure is not limited to these particular embodiments and contemplated embodiments with two or more flexible couplers, i.e., a plurality of flexible couplers, similar or dissimilar, and depending on the particular application.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A surgical construct comprising:
   a fixation device comprising a body with a first surface and an opposing second surface and two passages extending from the first surface to the opposing second surface; and
   a self-locking tensionable construct pre-loaded on the fixation device, the self-locking tensionable construct comprising two flexible couplers extending through the two passages of the fixation device and forming at least two flexible, closed, adjustable, knotless loops and a loop interconnection, wherein each of the two flexible couplers has two terminal ends, wherein one of the two terminal ends of each of the two flexible couplers is passed multiple times through the flexible coupler to each form an accordion-type weave region and a plurality of locking points, and wherein the one of the two terminal ends is connected to other of the two terminal ends of each of the two flexible couplers by a suture passing device.

2. The surgical construct of claim 1, wherein each of the two flexible couplers is suture tape and the fixation device is an implantable button.

3. The surgical construct of claim 1, wherein each accordion-type weave region is located between one of the two flexible, closed, adjustable, knotless loops and one of the two terminal ends.

4. The surgical construct of claim 1, wherein at least one of the fixation device and the two flexible couplers is visually coded.

5. The surgical construct of claim 1, wherein the fixation device is configured to be secured to bone, and the loop interconnection is configured to attach soft tissue to bone.

6. The surgical construct of claim 5, wherein the fixation device is configured to be pulled through a bone tunnel and exit a bone cortex to secure the soft tissue to bone.

7. The surgical construct of claim 5, wherein the bone is femur and the soft tissue is an ACL or PCL graft.

8. A surgical assembly comprising:
   a fixation device comprising a body with a first surface and an opposing second surface and two passages extending from the first surface to the opposing second surface; and
   a self-locking tensionable construct pre-loaded on the fixation device, the self-locking tensionable construct comprising two flexible couplers extending through the two passages of the fixation device and forming at least two flexible, closed, adjustable, knotless loops;
   wherein each of the two flexible couplers has two terminal ends, wherein one terminal end of each of the two flexible couplers is passed multiple times through respective flexible coupler to form an accordion-type weave region and a plurality of locking points, and the other terminal end of each of the two flexible couplers is attached to a needle.

9. The surgical assembly of claim 8, wherein each of the two flexible couplers is suture or suture tape, and the fixation device is an implantable button.

10. The surgical assembly of claim 8, further comprising an inserter.

11. A method of forming a knotless self-locking construct, comprising:
    passing a first flexible coupler and a second flexible coupler through passages of a fixation device to form at least two flexible, continuous, closed, adjustable, knotless loops, wherein each of the first and second flexible couplers has a first end and a second end;
    interconnecting the first flexible coupler with the second flexible coupler to form a loop interconnection, the loop interconnection separating the at least two flexible, continuous, closed, adjustable, knotless loops;
    passing one of the first end and the second end of each of the first and second flexible couplers through the flexible coupler multiple times to each form an accordion-type weave region and a plurality of locking points; and
    attaching the other of the first end and the second end of each of the first and second flexible couplers to a needle.

12. The method of claim 11, further comprising the step of adjusting the length of the at least two flexible, continuous, closed, adjustable, knotless loops to approximate first tissue to second tissue.

13. The method of claim 11, further comprising the steps of:
attaching the fixation device to an inserter;
passing the needle attached to each of the first and second flexible couplers through a first tissue to form a plurality of stitches;
inserting the fixation device into a second tissue and securing the fixation device to the second tissue; and
pulling on the first flexible coupler and the second flexible coupler to adjust tension of the at least two flexible, continuous, closed, adjustable, knotless loops, to approximate the first tissue to the second tissue and to bring the fixation device and the first tissue together.

14. The method of claim 11, wherein the first tissue is soft tissue and the second tissue is bone.

* * * * *